US009113972B2

(12) United States Patent
Trudeau

(10) Patent No.: US 9,113,972 B2
(45) Date of Patent: Aug. 25, 2015

(54) APPARATUS AND METHODS FOR IMMOBILIZATION AND FUSION OF A SYNOVIAL JOINT

(75) Inventor: Jeffrey L. Trudeau, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 98 days.

(21) Appl. No.: 13/594,555

(22) Filed: Aug. 24, 2012

(65) Prior Publication Data

US 2013/0053902 A1 Feb. 28, 2013

Related U.S. Application Data

(60) Provisional application No. 61/526,807, filed on Aug. 24, 2011.

(51) Int. Cl.
*A61B 17/84* (2006.01)
*A61B 17/88* (2006.01)
*A61B 17/68* (2006.01)
*A61B 17/86* (2006.01)

(52) U.S. Cl.
CPC ............ *A61B 17/844* (2013.01); *A61B 17/68* (2013.01); *A61B 17/864* (2013.01); *A61B 17/8685* (2013.01); *A61B 17/866* (2013.01); *A61B 17/8625* (2013.01); *A61B 2017/8655* (2013.01)

(58) Field of Classification Search
CPC ............. A61B 17/844; A61B 17/8685; A61B 2017/8655; A61B 17/846; A61B 17/8605; A61B 17/8625; A61B 17/863; A61B 17/864; A61B 17/742; A61B 17/74; A61B 17/746; F16B 13/068; F16B 13/124
USPC ...................................... 606/300–331; 411/32
See application file for complete search history.

(56) References Cited

U.S. PATENT DOCUMENTS

| 1,168,770 | A | * | 1/1916 | Wagner ......................... 411/80.1 |
| 3,739,684 | A | * | 6/1973 | Vitkevich ......................... 411/49 |
| 4,569,338 | A | | 2/1986 | Edwards |
| 4,800,874 | A | | 1/1989 | David et al. |
| 5,034,011 | A | | 7/1991 | Howland |
| 5,300,073 | A | | 4/1994 | Ray et al. |
| 5,334,205 | A | | 8/1994 | Cain |
| 5,643,264 | A | | 7/1997 | Sherman et al. |
| 5,713,904 | A | | 2/1998 | Errico et al. |
| 5,797,963 | A | * | 8/1998 | McDevitt ...................... 606/232 |

(Continued)

FOREIGN PATENT DOCUMENTS

| WO | 0158369 | 8/2001 |
| WO | 2006022644 | 3/2006 |

(Continued)

*Primary Examiner* — Michael T Schaper
*Assistant Examiner* — Amy Sipp
(74) *Attorney, Agent, or Firm* — Fitch, Even, Tabin & Flannery LLP

(57) ABSTRACT

Methods and apparatus for immobilizing a synovial joint, such as a sacroiliac (SI) joint are disclosed. In one form, a multipiece fixation device, such as a dowel, includes multiple expandable fasteners that are configured to fix adjacent bones of a synovial joint with respect to one another. The expandable fasteners include expansion portions that are expanded radially via insertion of another expandable fastener or an expansion device to fix the expandable fasteners to the bone. The fixation device may be configured to provide for compression or distraction of the bones of the synovial joint while at the same time stabilizing the joint.

9 Claims, 14 Drawing Sheets

(56) References Cited

U.S. PATENT DOCUMENTS

| | | | |
|---|---|---|---|
| 6,053,916 A | 4/2000 | Moore | |
| 6,565,566 B1 | 5/2003 | Wagner et al. | |
| 6,635,059 B2 | 10/2003 | Randall et al. | |
| 6,905,512 B2 | 6/2005 | Paes et al. | |
| 6,951,561 B2 * | 10/2005 | Warren et al. | 606/328 |
| 7,261,505 B2 | 8/2007 | Ernst et al. | |
| 7,648,509 B2 | 1/2010 | Stark | |
| 7,717,958 B2 | 5/2010 | Cragg et al. | |
| 7,833,246 B2 | 11/2010 | Mitchell | |
| 7,850,732 B2 | 12/2010 | Heinz | |
| 7,857,840 B2 * | 12/2010 | Krebs et al. | 606/327 |
| 7,909,871 B2 | 3/2011 | Abdou | |
| 7,922,765 B2 | 4/2011 | Reiley | |
| 7,938,834 B2 | 5/2011 | Roush | |
| 8,221,479 B2 * | 7/2012 | Glazer et al. | 606/326 |
| 8,449,583 B2 * | 5/2013 | Krebs et al. | 606/300 |
| 8,690,917 B2 * | 4/2014 | Suh et al. | 606/246 |
| 2002/0049447 A1 * | 4/2002 | Li | 606/73 |
| 2005/0143735 A1 * | 6/2005 | Kyle | 606/60 |
| 2006/0149258 A1 * | 7/2006 | Sousa | 606/72 |
| 2006/0195103 A1 * | 8/2006 | Padget et al. | 606/72 |
| 2007/0213732 A1 * | 9/2007 | Khanna et al. | 606/73 |
| 2008/0021454 A1 | 1/2008 | Chao et al. | |
| 2008/0021456 A1 | 1/2008 | Gupta et al. | |
| 2008/0140082 A1 | 6/2008 | Erdem et al. | |
| 2008/0188897 A1 * | 8/2008 | Krebs et al. | 606/300 |
| 2009/0024174 A1 | 1/2009 | Stark | |
| 2009/0036927 A1 | 2/2009 | Vestgaarden | |
| 2009/0099610 A1 | 4/2009 | Johnson et al. | |
| 2009/0131986 A1 | 5/2009 | Lee et al. | |
| 2009/0138053 A1 | 5/2009 | Assell et al. | |
| 2009/0216238 A1 | 8/2009 | Stark | |
| 2009/0259261 A1 | 10/2009 | Reiley | |
| 2009/0281580 A1 * | 11/2009 | Emannuel | 606/304 |
| 2009/0287254 A1 | 11/2009 | Nayet et al. | |
| 2010/0003102 A1 * | 1/2010 | Nagaiwa et al. | 411/80.1 |
| 2010/0010496 A1 | 1/2010 | Isaza et al. | |
| 2010/0106200 A1 | 4/2010 | Stark | |
| 2010/0131011 A1 | 5/2010 | Stark | |
| 2010/0198267 A1 | 8/2010 | Vaidya | |
| 2010/0268228 A1 | 10/2010 | Petersen | |
| 2011/0040362 A1 | 2/2011 | Godara et al. | |
| 2011/0054373 A1 | 3/2011 | Reiley | |
| 2011/0087294 A1 | 4/2011 | Reiley | |
| 2011/0087296 A1 | 4/2011 | Reiley et al. | |
| 2011/0098816 A1 | 4/2011 | Jacob et al. | |
| 2011/0098817 A1 | 4/2011 | Eckhardt et al. | |
| 2011/0118785 A1 | 5/2011 | Reiley | |
| 2011/0118790 A1 | 5/2011 | Reiley | |
| 2011/0118841 A1 | 5/2011 | Reiley | |
| 2011/0144766 A1 | 6/2011 | Kale et al. | |
| 2011/0160772 A1 | 6/2011 | Arcenio et al. | |
| 2011/0166602 A1 | 7/2011 | Malek | |
| 2011/0184472 A1 * | 7/2011 | Niederberger et al. | 606/304 |
| 2011/0319946 A1 * | 12/2011 | Levy et al. | 606/309 |
| 2012/0172934 A1 | 7/2012 | Fisher et al. | |
| 2012/0191191 A1 * | 7/2012 | Trieu | 623/17.11 |

FOREIGN PATENT DOCUMENTS

| | | |
|---|---|---|
| WO | 2009029074 | 3/2009 |
| WO | 2010065015 | 6/2010 |
| WO | 2011014135 | 2/2011 |

* cited by examiner

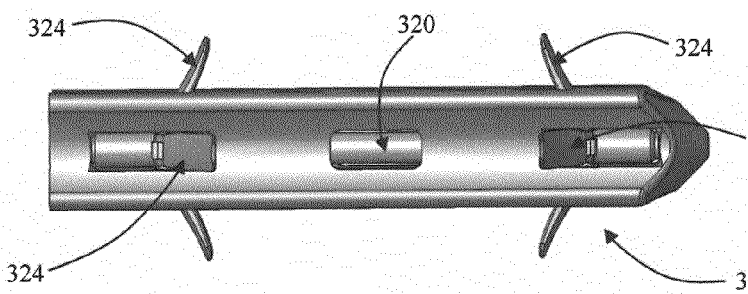
FIG. 8
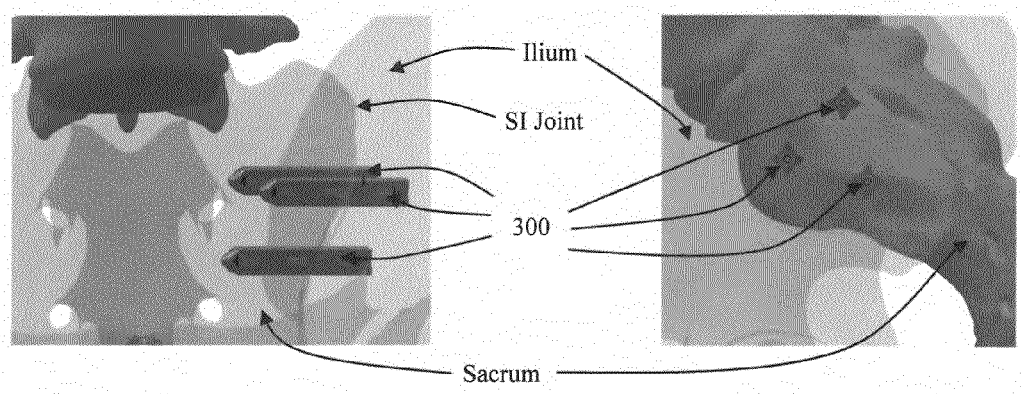
FIG. 9A
FIG. 9B
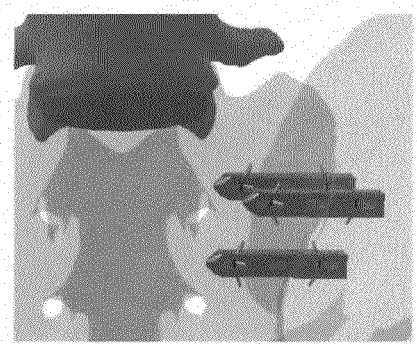
FIG. 10A
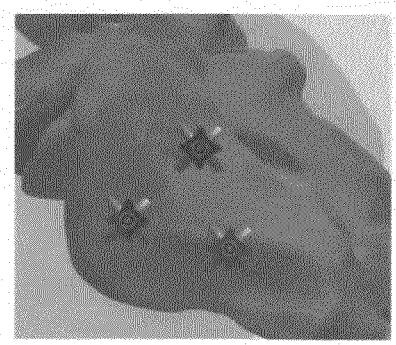
FIG. 10B

APPARATUS AND METHODS FOR IMMOBILIZATION AND FUSION OF A SYNOVIAL JOINT

CROSS-REFERENCE TO RELATED APPLICATION

This application claims the benefit of U.S. Provisional Application No. 61/526,807, filed Aug. 24, 2011, which is hereby incorporated herein by reference in its entirety.

FIELD OF THE INVENTION

The present invention relates to the immobilization and fusion of a synovial joint and, more particularly, to apparatus and methods for the immobilization and fusion of the sacroiliac joint.

BACKGROUND OF THE INVENTION

The sacroiliac joint is a synovial joint between the sacrum, which is the inferior (or caudal) terminus of the spinal column, and the ilium of the pelvis. As with other synovial joints, the sacroiliac joint (or "SI" joint) can degenerate and undergo degenerative arthritic changes due to a number of possible causes, including trauma to the joint or the hypermobility induced in the joint during childbirth. The degenerated SI joint loses stability and experiences non-normal movements, resulting in an inflammatory response and subsequent pain. It has been reported that disorders of the SI joint are the source of back pain for up to 25% of patients (Cohen, 2005).

It is accepted practice to treat certain degenerated synovial joints, which normally exhibit low relative motions between the joint surfaces such as the spinal vertebral disc and SI joint, by stabilizing the joint through immobilization and subsequent bony fusion (arthrodesis). It is thought that eliminating relative movement of the joint surfaces will eliminate subsequent inflammation and pain. Surgical arthrodesis of the SI joint was first reported by Smith-Petersen and Rodgers in 1926 and is still performed today. Arthrodesis is performed by inducing growth of bone between the joint surfaces to fuse the joint, first by removal of all of the soft tissue of the joint to eliminate any barriers to bone tissue formation, followed by scraping of the bony joint surfaces to induce bleeding and the subsequent biological response of bone formation, and often with filling the prepared joint with morselized bone to assist in the bone formation process. Immobilizing the joint as part of the arthrodesis procedure provides immediate stability to the joint and reduction of the pain-generating movement, and allows quicker bone formation.

Immobilization of the SI joint has historically been performed by placing one or more, simple threaded screws through the joint, normal to the general plane of the joint. Due to variations in bone density and/or morphology between individual patients, as well as occasional bone removal from the ilium from previous spinal fusion surgeries, simple threaded screws are often insufficient to provide the joint stability required for a successful arthrodesis procedure. There exists a need for improved designs that can offer improved ability to immobilize the SI joint in more patients and reduce the risk of back-out of the fixation device.

BRIEF DESCRIPTION OF THE DRAWINGS

To understand the present invention, it will now be described by way of example, with reference to the accompanying drawings in which:

FIG. 8 is a side elevation view of the dowel shown in FIG. 7;

FIGS. 9A and 9B are anterior and lateral views of a plurality of dowels according to the embodiment shown in FIG. 5 implanted within the SI joint;

FIGS. 10A and 10B are anterior and lateral views of a plurality of dowels according to the embodiment shown in FIG. 7 implanted within the SI joint;

DETAILED DESCRIPTION OF THE PREFERRED EMBODIMENTS

Figures 1A, 1B:
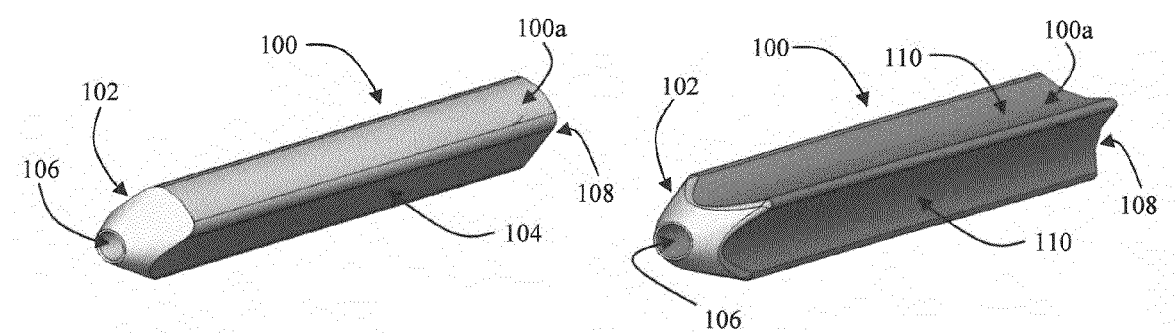
FIG. 1A is a perspective view of a dowel according to the present invention.
FIG. 1B is a perspective view of an alternate embodiment of a dowel according to the present invention.

A single-piece, solid non-threaded device or connector for joint fixation in the form of dowel 100 for being implanted singly or in multiples, is shown in FIGS. 1A, 1B, 2A and 2B. As shown in FIG. 1A, dowel 100 has an elongate body 100a having a distal or leading end 102 configured to assist insertion into a pre-drilled hole through the SI joint surfaces. As illustrated, the distal end 102 can be tapered for ease of insertion. The body 100a of the dowel 100 has a proximal end 108 configured for receiving an impact force. Referring to FIG. 3B, the proximal end 108 has a relatively blunt or flat configuration for being contacted with a mallet or other insertion instrument. The dowel body 100a may be configured with cannula 106, which is a hole bored generally along the longitudinal axis of dowel body 100a to facilitate the use of a guide pin (not shown) intended to aid in placement of dowel 100 into a pre-drilled hole through the SI joint surfaces.

Dowel body 100a can have an outer surface that has a non-circular cross-sectional configuration. In this regard, the elongate body 100a can include a longitudinal flat surface 104. The non-round profile aids in avoiding rotation of the SI joint surfaces around the long axis of the implanted dowel 100, providing further stabilization of the joint. Dowel body 100a may have a single or multiple flat surfaces 104, producing a generally rectangular cross-sectional shape with two flat surfaces 104, a generally triangular cross-sectional shape with three flat surfaces 104, etc. Instead of flat surfaces 104, dowel body 100a may have one or more longitudinal concave surfaces 110 as shown in FIG. 1B. These concave surfaces 110 provide additional contact area with the surrounding bone and may offer improved rotational resistance. The flat surfaces 104 and concave surfaces 110 extend along the length of the elongate dowel body 100a at least sufficient to engage the bone of the sacrum and ilium. Flat surfaces 104, concave surfaces 110, and other non-round surface profiles can be combined to provide specific desired cross-sectional profiles as well as a flexural stiffness for dowel 100 that varies depending on the direction of applied force.

Dowel body 100a may be made of any biologically inert material with sufficient strength, toughness and other material properties appropriate for use in joint stabilization, including (but not limited to) plastics, metals, ceramics, human cadaver donor bone and bone analogues such as coral-derived hydroxyapatite. Suitable plastics include polyether-ether-ketone (PEEK), polyether-ketone-ketone (PEKK) and other related polyaryls, which may be combined with carbon fiber or other fillers to form composites with enhanced material properties. These polymers and composites are often well-suited for joint stabilization due to their modulus of elasticity which is similar to the surrounding bone, which reduces the potential for stress-shielding that might occur with stiffer materials. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for dowel 100. The outer surface of dowel body 100a may be modified to enable and/or promote bony tissue in-growth into dowel body 100a. Surface enhancements may include a roughened surface, or application of a porous (open-pore) version of the dowel 100 substrate material to enable bony in-growth such as porous PEEK or sintered titanium. Other surface enhancements can include application of a non-similar material such as hydroxyapatite.

Figures 2A, 2B:
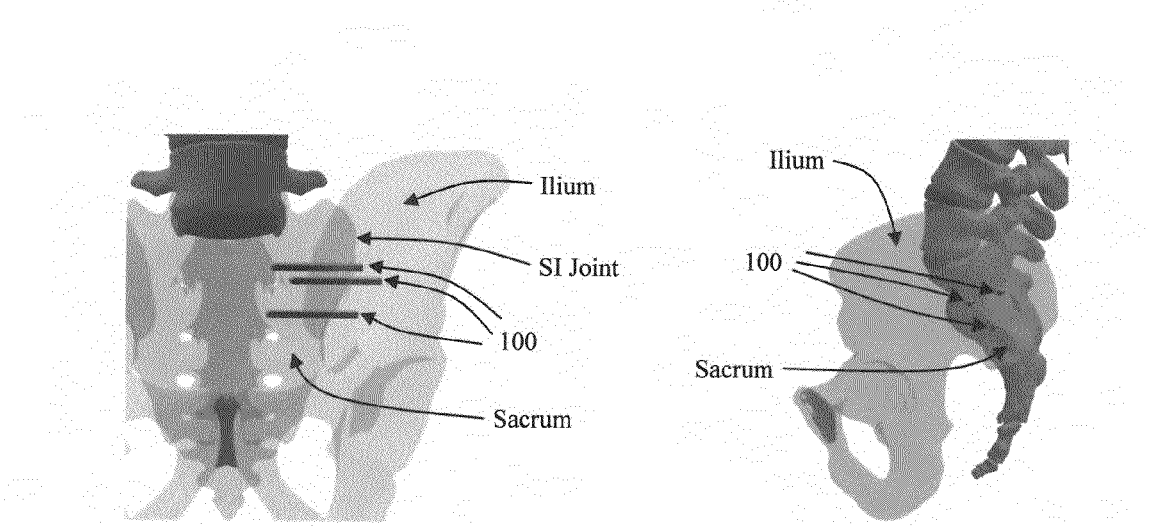
FIG. 2A is an anterior view of a plurality of dowels according to the present invention implanted within the SI joint.
FIG. 2B is a lateral view of a plurality of dowels according to the present invention implanted within the SI joint.

Illustrations showing one example of one embodiment of dowel 100 implanted in a patient are shown in FIGS. 2A and 2B. FIG. 2A is an anterior (front) view and FIG. 2B is a lateral (side) view, and are similar to what might be seen on a diagnostic image (x-ray, computed tomography (CT) scan or magnetic resonance image (MRI) scan) of an implanted patient. While this example shows the use of three dowels 100, more or fewer dowels 100 may be utilized depending on individual patient needs.

Figure 3A:
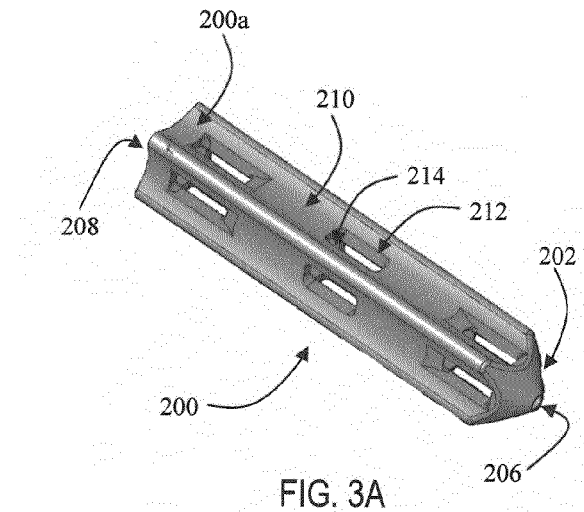
FIG. 3A is a perspective view of an alternate embodiment of a dowel according to the present invention.
Figure 3B:
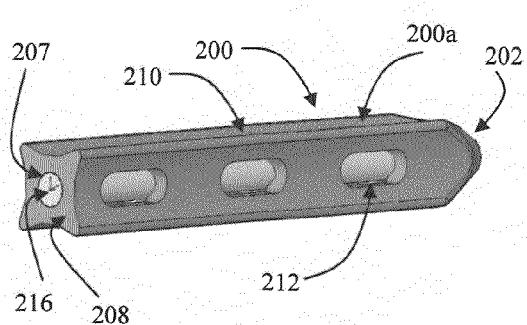
FIG. 3B is a perspective view of the dowel of FIG. 3A including a central pin.

Another joint fixation device or connector in the form of dowel 200 is provided. Dowel 200 has no external screw threads and a hollow inner chamber 214, can be implanted singly or in multiples, and is shown in FIGS. 3A, 3B, 4A and 4B. As shown in FIG. 3A, similar to dowel 100, dowel 200 has an elongate body 200a having a relatively tapered distal end 202 to assist insertion into a pre-drilled hole through the SI joint surfaces and a relatively blunt proximal end 208 configured for contact with a mallet or other insertion instrument. The dowel body 200a may be configured with cannula 206, which is a hole bored generally along the longitudinal axis of dowel 200 to facilitate the use of a guide pin (not shown) intended to aid in placement of dowel 200 into a pre-drilled hole through the SI joint surfaces.

The dowel body 200a also can have another surface with a non-circular configuration such as due to the presence of longitudinal concave surfaces 210. The non-round profile aids in avoiding rotation of the SI joint surfaces around the long axis of the implanted dowel 200a, providing further stabilization of the joint. The dowel body 200a may have a single or multiple concave surfaces 210, producing a generally rectangular cross-sectional shape with two concave surfaces 210, a generally triangular cross-sectional shape with three concave surfaces 210, etc. Instead of concave surfaces 210, dowel body 200a may have one or more longitudinal flat surfaces 104 as shown in FIG. 1A. The flat surfaces 104 and concave surfaces 210 extend along the length of the elongate dowel body 200a at least sufficient to engage the bone of the sacrum and ilium. Flat surfaces 104, concave surfaces 210, and other non-round surface profiles can be combined to provide specific desired cross-sectional profiles as well as a flexural stiffness for dowel 200 that varies depending on the direction of applied force.

Dowel body 200a is configured with side holes 212 that extend transverse to the longitudinal axis of the body 200a to open to both the outer surface 210 and the inner chamber 214. The embodiment shown in FIGS. 3A and 3B shows three oval shaped or rectangular shaped side holes 212 on each of the sides of dowel body 200a, but other quantities and other shapes of side holes 212 could be used. Side holes 212 are intended to offer the surgeon the option to pack the inner chamber 214 and side holes 212 of dowel 200 with morselized autologous bone, demineralized donor bone product, or bone analogue, with or without bone growth proteins in order to aid new bone growth in general and interlocking bone growth in particular.

Dowel body 200a may be configured with an inner chamber 214 and proximal hole 207 to accommodate a central pin 216. Central pin 216 can be inserted in proximal hole 207 and secured within chamber 214 in order to stiffen dowel 200 if necessary. Central pin 216 and proximal hole 207 may be configured with complementary screw threads, slots, barbs, or other mechanical structural features for retention of central pin 216 within dowel body 200a. Side holes 212 can be filled with bone or bone analogue, and allow interlocking bone growth even with central pin 216 in place. In one embodiment, dowel body 200a made from PEEK, with a large inner chamber 214 and multiple large side holes 212 may benefit from insertion of central pin 216 made from a titanium alloy to provide sufficient overall stiffness to adequately stabilize the SI joint.

Dowel 200 and central pin 216 may be made of any biologically inert material with sufficient strength, toughness and other material properties appropriate for use in joint stabilization, including (but not limited to) plastics, metals, ceramics, human cadaver donor bone and bone analogues such as coral-derived hydroxyapatite. Suitable plastics include polyether-ether-ketone (PEEK), polyether-ketone-ketone (PEKK) and other related polyaryls, which may be combined with carbon fiber or other fillers to form composites with enhanced material properties. These polymers and composites are often well-suited for joint stabilization due to their modulus of elasticity which is similar to the surrounding bone, which reduces the potential for stress-shielding that might occur with stiffer materials. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for dowel 200 and central pin 216. The outer surface of dowel 200 and/or central pin 216 may be modified to enable and/or promote bony tissue in-growth into dowel 200 and/or central pin 216. Surface enhancements may include a roughened surface, or application of a porous (open-pore) version of the underlying surface material to enable bony in-growth such as porous PEEK or sintered titanium. Other surface enhancements can include application of a non-similar material such as hydroxyapatite.

Figure 4A:
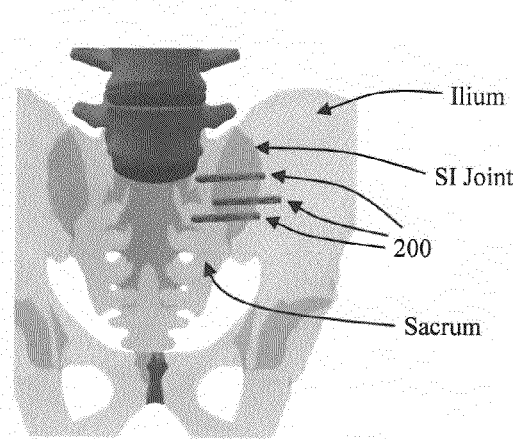
FIG. 4A is an anterior view of a plurality of dowels according to the embodiment shown in FIG. 3A implanted within the SI joint.
Figure 4B:
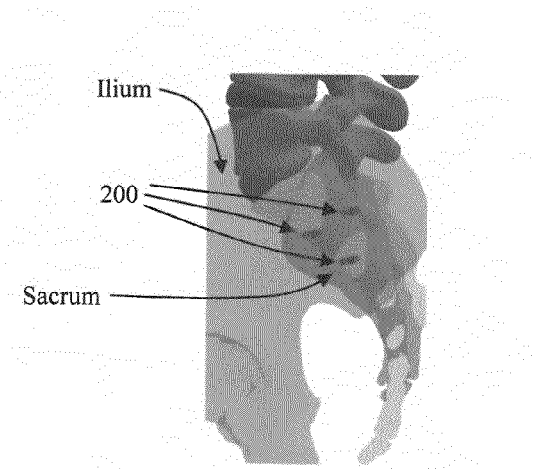
FIG. 4B is a lateral view of the plurality of dowels shown in FIG. 4A.

Illustrations showing one example of one embodiment of dowel 200, without the central pin 216, implanted in a patient are shown in FIGS. 4A and 4B. FIG. 4A is an anterior (front) view and FIG. 4B is a lateral (side) view, and are similar to what might be seen on a diagnostic image (x-ray, computed tomography (CT) scan or magnetic resonance image (MRI) scan) of an implanted patient. While this example shows the use of three dowels 200, more or fewer dowels 200 may be implanted depending on individual patient needs.

Figure 5:
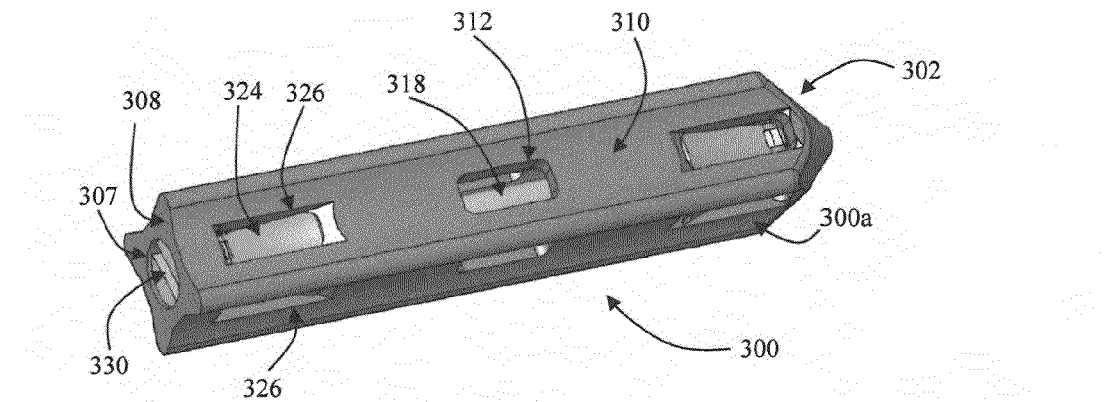
FIG. 5 is a perspective view of a dowel according to the present invention.
Figure 6:
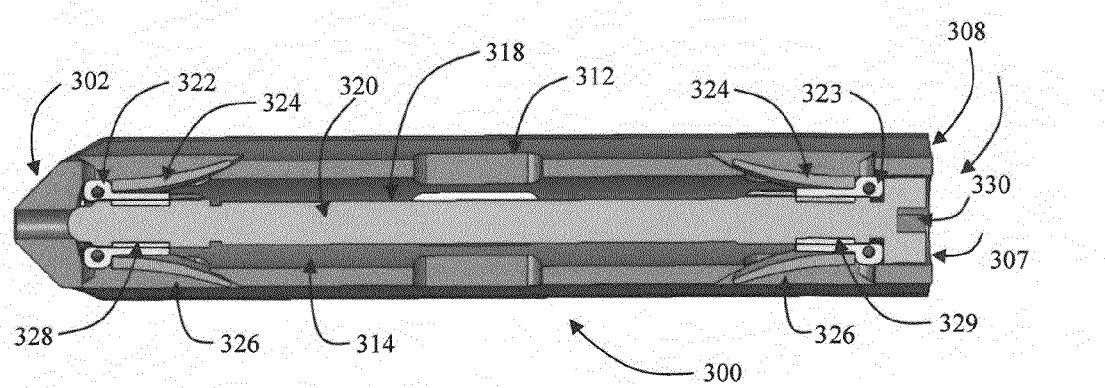
FIG. 6 is a vertical cross-sectional view of the dowel of FIG. 5 taken along the longitudinal axis thereof.
Figure 7:
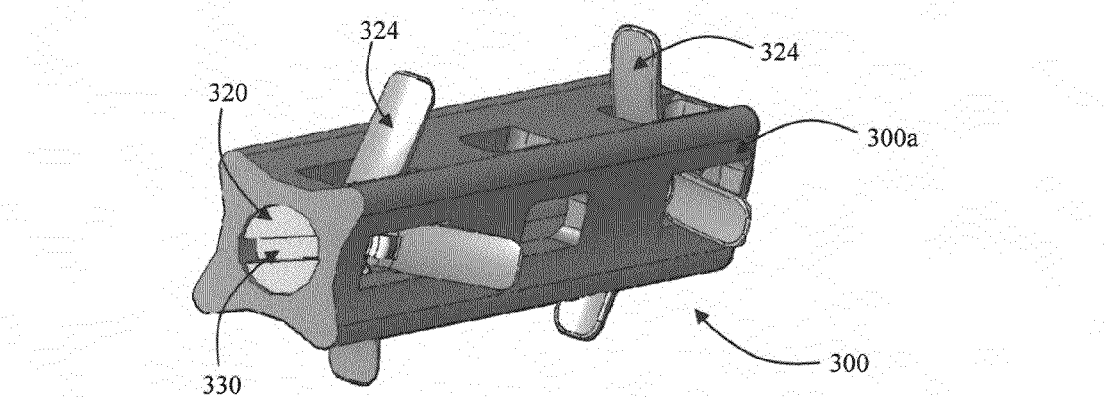
FIG. 7 is a perspective view of the dowel of FIG. 5 showing the paddle members extended.

Another joint fixation device or connector in the form of dowel 300 is provided. Dowel 300 has no external threads and a hollow inner chamber 314, can be implanted singly or in multiples, and is shown in FIGS. 5-8, 9A, 9B, 10A and 10B. As shown in FIG. 5 similar to dowels 100 and 200, dowel 300 has an elongate body 300a having a relatively tapered distal end 302 to assist insertion into a pre-drilled hole through the SI joint surfaces and a relatively blunt proximal end 308 configured for contact with a mallet or other insertion instrument.

The dowel body 300a also can have an outer surface with a non-circular configuration such as due to the presence of longitudinal concave surfaces 310 that extend axially or longitudinally therealong. The non-round profile aids in avoiding rotation of the SI joint surfaces around the long axis of the implanted dowel 300, providing further stabilization of the joint. The dowel body 300a may have a single or multiple concave surfaces 310, producing a generally rectangular cross-sectional shape with two concave surfaces 310, a generally triangular cross-sectional shape with three concave surfaces 310, etc. Instead of concave surfaces 310, dowel body 300a may have one or more longitudinal flat surfaces 104 as shown in FIG. 1A. The flat surfaces 104 and concave surfaces 310 extend along the length of the elongate dowel body 300a at least sufficient to engage the bone of the sacrum and ilium. Flat surfaces 104, concave surfaces 310, and other non-round surface profiles can be combined to provide specific desired cross-sectional profiles as well as a flexural stiffness for dowel 300 that varies depending on the direction of applied force.

Dowel body 300a is configured with side holes 312 positioned in the central portion of dowel 300 that extend transverse to the length of the body 300a to open to both outer surface 310 and the inner chamber 314. The embodiment shown in FIGS. 5, 6, 7 and 8 shows one rectangular shaped side hole 312 on each of the sides of the dowel body 300a, but other quantities and other shapes of side holes 312 could be used. Side holes 312 are intended to offer the surgeon the option to pack the inner chamber 314 and side holes 312 of dowel 300 with morselized autologous bone, demineralized donor bone product, or bone analogue, with or without bone growth proteins in order to aid new bone growth in general and interlocking bone growth in particular.

Dowel 300 is configured with an inner chamber 314 and proximal hole 307 sized to contain compression assembly 318 in a non-operative configuration. Compression assembly 318 consists of an actuator in the form of a central pin 320, having a region with a right-handed RH screw thread 328 located at the distal tip of central pin 320 and a region with a left-handed LH screw thread 329 located at the proximal tip of central pin 320. Right-handed RH threaded sleeve 322 has a right-handed screw thread on the internal surface of the sleeve, and is movably attached to the distal tip of central pin 320 such that the threads of RH threaded sleeve 322 engage RH screw thread 328. Left-handed LH threaded sleeve 323 has a left-handed screw thread on the internal surface of the sleeve, and is movably attached to the proximal tip of central pin 320 such that the threads of LH threaded sleeve 323 engages LH screw thread 329. Extendable anchor members such as paddles 324 are attached to RH threaded sleeve 322 and LH threaded sleeve 323 such that they are allowed to pivot with respect to the longitudinal axis of dowel 300, and positioned within projection holes 326. Projection holes 326 connect outer surface 310 with inner chamber 314. A cam surface is disposed at the medial edge of the holes 326 and is configured to form an upward-angled medial edge cam surface such that longitudinal movement of paddles 324 toward and along the cam surface causes paddles 324 to pivot away, and extend radially outward, from dowel body 300a. Paddles 324 are shown in retracted position in FIGS. 5 and 6, and in extended position in FIGS. 7 and 8. Extension of paddles 324 is accomplished by rotating central pin 320 in a paddle actuating direction using an instrument such as a standard screwdriver designed to engage drive slot 330 in the head of the actuator pin 320. Drive slot 330 can alternatively be configured to accommodate other engagement instruments such as hex wrenches, box wrenches, Torx wrenches, Allen wrenches, or similar designs.

Paddles 324 at the proximal end of dowel 300 are intended to engage the surface of the ilium on the exterior of the SI joint and paddles 324 at the distal end of dowel 300 are intended to engage the surface of the sacrum on the exterior of the SI joint, once dowel 300 has been positioned within the pre-drilled hole through the SI joint surfaces and paddles 324 have been extended via rotation of central pin 320. Continued rotation of central pin 320 following bone engagement by paddles 324 will urge the joint surfaces toward each other to impart a compression force to the SI joint, with the intent of stabilizing the SI joint by compressing the joint surfaces against each other to minimize motion therebetween.

Illustrations showing one example of one embodiment of dowel 300 implanted with paddles in retracted and extended positions are shown in FIGS. 9A, 9B, 10A and 10B. While this example shows the use of three dowels 300, with four paddles 324 at each end of dowel 300, it should be understood that more or fewer dowels 300 may be implanted depending on individual patient needs and that dowel 300 may be designed with more or fewer paddles at each end.

Dowel 300 and the components of compression assembly 318 may be made of any biologically inert material with sufficient strength, toughness and other material properties appropriate for their function and use in joint stabilization, including (but not limited to) plastics, metals and ceramics. Suitable plastics include polyether-ether-ketone (PEEK), polyether-ketone-ketone (PEKK) and other related polyaryls, which may be combined with carbon fiber or other fillers to form composites with enhanced material properties. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for dowel 300 and compression assembly 318. Human cadaver donor bone and bone analogues such as coral-derived hydroxyapatite can be used for dowel 300. The outer surface of dowel 300 and at least portions of compression assembly 318 may be modified to enable and/or promote bony tissue in-growth into those surfaces. Surface enhancements may include a roughened surface, or application of a porous (open-pore) version of the underlying material to dowel 300 to enable bony in-growth such as porous PEEK or sintered titanium. Other surface enhancements can include application of a non-similar material such as hydroxyapatite.

Figure 11:
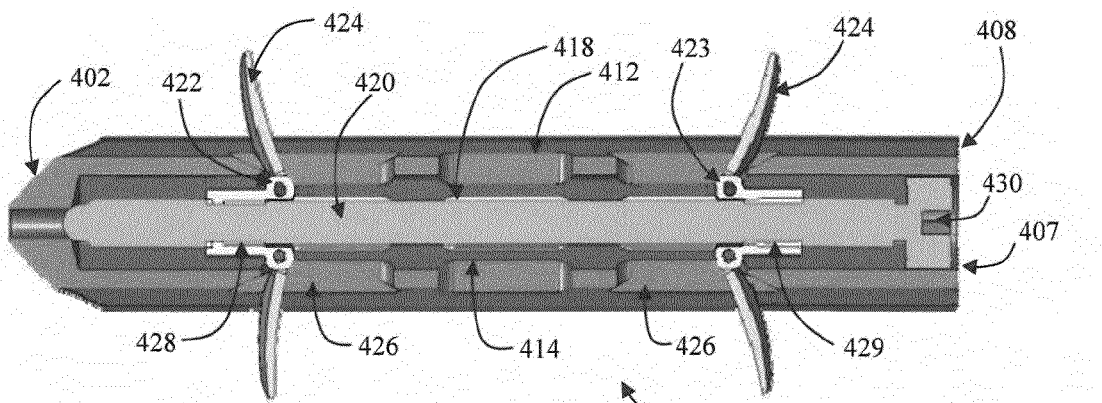
FIG. 11 is a vertical cross-sectional view of the dowel of FIG. 12 taken along the longitudinal axis thereof.
Figure 12:
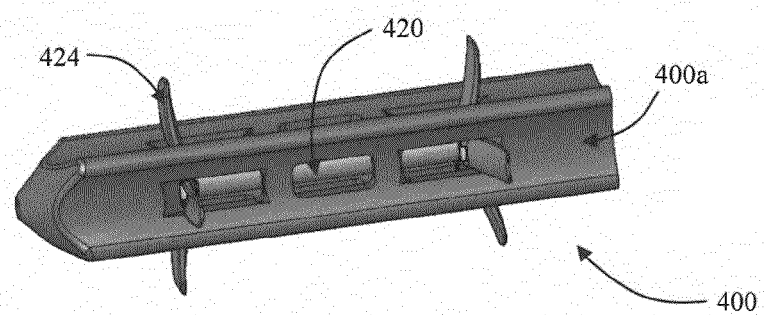
FIG. 12 is a perspective view of an alternate embodiment of a dowel according to the present invention showing the paddle members extended.
Figure 13:
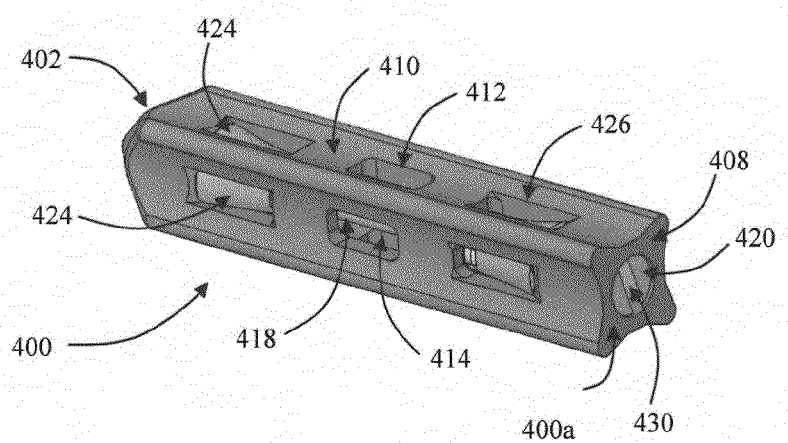
FIG. 13 is a perspective view of the dowel of FIG. 12 with the paddle members retracted.

Another joint fixation device or connector in the form of dowel 400 is provided. Dowel 400 has no external threads and a hollow inner chamber 414, can be implanted singly or in multiples, and is shown in FIGS. 11-13, 14A and 14B. As shown in FIG. 11, similar to the previously-described dowels 100-300, dowel 400 has an elongate body 400a having a relatively tapered distal end 402 to assist insertion into a pre-drilled hole through the SI joint surfaces and a relatively blunt proximal end 408 configured for contact with a mallet or other insertion instrument.

The dowel body 400a also can have an outer surface with a non-circular configuration such as due to the presence of longitudinal concave surfaces 410 that extend axially or longitudinally therealong. The non-round profile aids in avoiding the rotation of the SI joint surfaces around the long axis of the implanted dowel 400, providing further stabilization of the joint. The dowel body 400a may have a single or multiple concave surfaces 410, producing a generally rectangular cross-sectional shape with two concave surfaces 410, a generally triangular cross-sectional shape with three concave surfaces 410, etc. Instead of concave surfaces 410, dowel body 400a may have one or more longitudinal flat surfaces 104 as shown in FIG. 1A. The flat surfaces 104 and concave surfaces 410 extend along the length of the elongate dowel body 400a at least sufficient to engage the bone of the sacrum and ilium. Flat surfaces 104, concave surfaces 410, and other non-round surface profiles can be combined to provide specific desired cross-sectional profiles as well as a flexural stiffness for dowel 400 that varies depending on the direction of applied force.

Dowel body 400a is configured with side holes 412 positioned in the central portion of dowel 400 that extend transverse to the length of the body 400a to open to both outer surface 410 and the inner chamber 414. The embodiment shown in FIGS. 11, 12, 13, 14A and 14B shows one rectangular shaped side hole 412 on each of the sides of the dowel body 400a, but other quantities and other shapes of side holes 412 could be used. Side holes 412 are intended to offer the surgeon the option to pack the inner chamber 414 and side holes 412 of dowel 400 with morselized autologous bone, demineralized donor bone product, or bone analogue, with or without bone growth proteins in order to aid new bone growth in general and interlocking bone growth in particular.

Dowel 400 is configured with an inner chamber 414 and proximal hole 407 sized to contain distraction assembly 418 in a non-operative configuration. Distraction assembly 418 consists of an actuator in the form of a central pin 420, having a region with a right-handed RH screw thread 428 located distal to the medial portion of central pin 420 and a region with a left-handed LH screw thread 429 located proximal to the medial portion of central pin 420. Right-handed RH threaded sleeve 422 has a right-handed screw thread on the internal surface of the sleeve, and is movably attached to central pin 420 distal to the medial portion of central pin 420 such that the threads of RH threaded sleeve 422 engage RH screw thread 428. Left-handed LH threaded sleeve 423 has a left-handed screw thread on the internal surface of the sleeve, and is movably attached to central pin 420 proximal to the medial portion of central pin 420 such that the threads of LH threaded sleeve 423 engages LH screw thread 429. Extendable anchor members such as paddles 424 are attached to RH threaded sleeve 422 and LH threaded sleeve 423 such that they are allowed to pivot with respect to the longitudinal axis of dowel 400, and positioned within projection holes 426. Projection holes 426 connect outer surface 410 with inner chamber 414. A cam surface is disposed at the medial edge of the holes 426 and is configured to form an upward-angled edge opposite the medial edge cam surface such that longitudinal movement of paddles 424 toward and along the cam surface laterally from the medial location causes paddles 424 to pivot away, and extend outward, from dowel body 400a. Paddles 424 are shown in extended position in FIGS. 11 and 12, and in retracted position in FIG. 13. Extension of paddles 424 is accomplished by rotating central pin 420 in a paddle actuating direction using a drive instrument such as a standard screwdriver designed to engage drive slot 430 in the head of the actuator pin 420. Drive slot 430 can alternatively be configured to accommodate other engagement instruments such as hex wrenches, box wrenches, Torx wrenches, Allen wrenches, or similar designs.

Paddles 424 proximal to the medial portion of dowel 400 are intended to engage the surface of the ilium within the interior of the SI joint and paddles 424 distal to the medial portion of dowel 400 are intended to engage the surface of the sacrum within the interior of the SI joint, once dowel 400 has been positioned within the pre-drilled hole through the SI joint surfaces and paddles 424 have been extended via rotation of central pin 420. Continued rotation of central pin 420 following bone engagement by paddles 424 will urge the joint surfaces apart to impart a distraction force to the SI joint, with the intent of stabilizing the SI joint by distracting the joint and inducing tension in the ligaments connecting the ilium and sacrum.

Figures 14A, 14B:
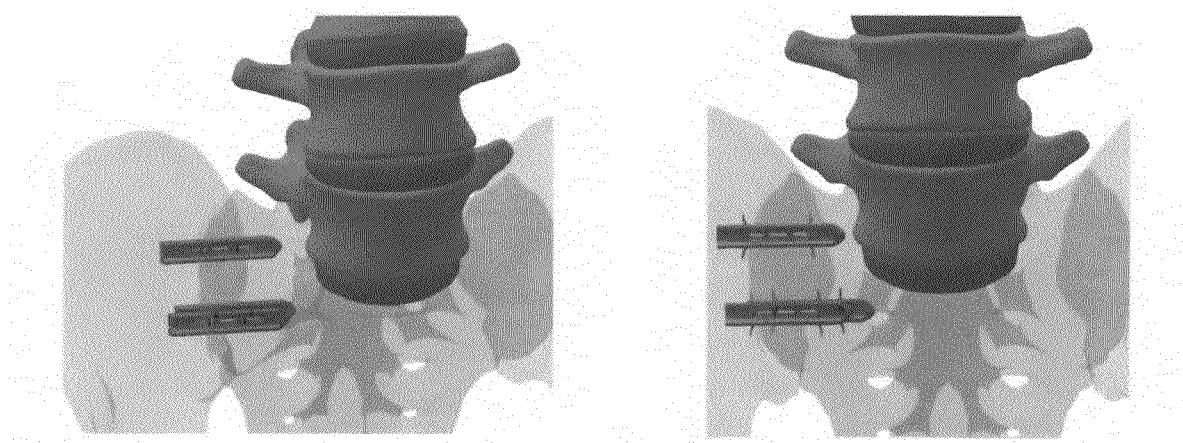
FIGS. 14A and 14B are anterior views of a plurality of dowels according to the embodiment of FIG. 12 implanted within the SI joint showing the paddle members retracted and extended, respectively.

Illustrations showing one example of one embodiment of dowel 400 implanted with paddles in retracted and extended positions are shown in FIGS. 14A and 14B. While this example shows the use of three dowels 400, with four paddles 424 at each end of dowel 400, it should be understood that more or fewer dowels 400 may be implanted depending on individual patient needs and that dowel 400 may be designed with more or fewer paddles at each end.

Dowel 400 and the components of distraction assembly 418 may be made of any biologically inert material with sufficient strength, toughness and other material properties appropriate for their function and use in joint stabilization, including (but not limited to) plastics, metals and ceramics. Suitable plastics include polyether-ether-ketone (PEEK), polyether-ketone-ketone (PEKK) and other related polyaryls, which may be combined with carbon fiber or other fillers to form composites with enhanced material properties. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for dowel 400 and compression assembly 418. Human cadaver donor bone and bone analogues such as coral-derived hydroxyapatite can be used for dowel 400. The outer surface of dowel 400 and at least portions of compression assembly 418 may be modified to enable and/or promote bony tissue in-growth into those surfaces. Surface enhancements may include a roughened surface, or application of a porous (open-pore) version of the underlying material to dowel 400 to enable bony in-growth such as porous PEEK or sintered titanium. Other surface enhancements can include application of a non-similar material such as hydroxyapatite.

An alternative joint fixation device or connector described below provides a distraction force to the SI joint for stabilization, similar to dowel 400, but does so with only one set of paddles instead of two.

Figure 15:
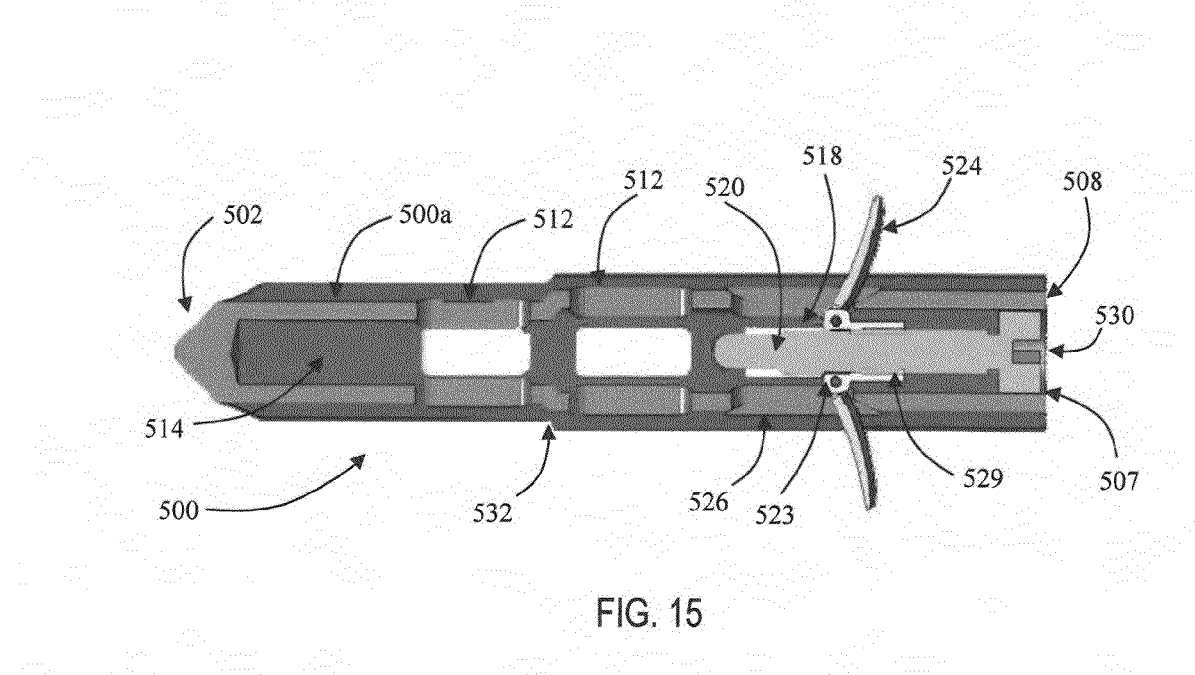
FIG. 15 is a vertical cross-sectional view of the dowel of FIG. 16 taken along the longitudinal axis thereof.
Figure 16:
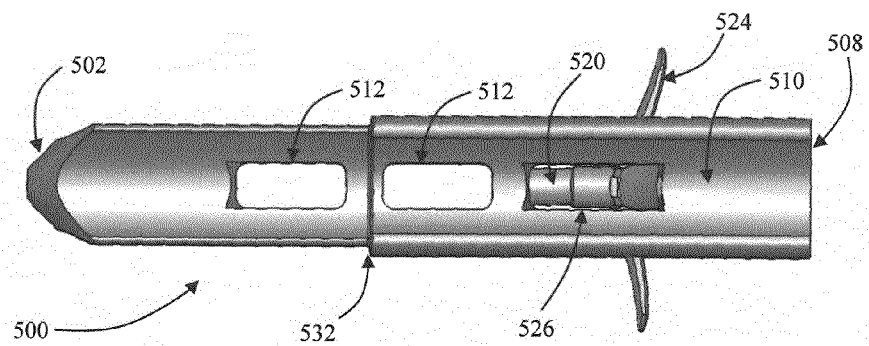
FIG. 16 is a perspective view of an alternate embodiment of a dowel according to the present invention showing the paddle members extended.
Figure 17:
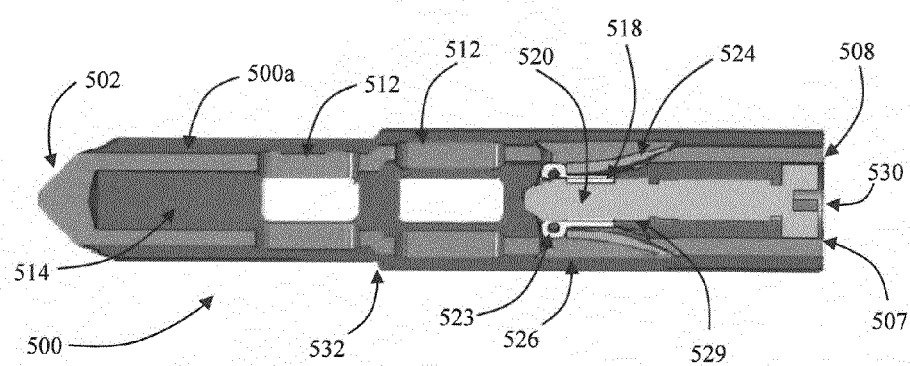
FIG. 17 is a vertical cross-sectional view of the dowel of FIG. 16 with the paddle members retracted.

The alternative joint fixation device or connector can also be in the form of dowel 500. Dowel 500 has no external threads and a hollow inner chamber 514, can be implanted singly or in multiples, and is shown in FIGS. 15-17, 18A and 18B. As shown in FIG. 15, similar to previously described dowels, dowel 500 has an elongate body 500a having a relatively tapered distal end 502 to assist insertion into pre-drilled holes through the SI joint surfaces and a relatively blunt proximal end 508 configured for contact with a mallet or other insertion instrument.

The dowel body 500a also can have an outer surface with a non-circular configuration such as due to the presence of longitudinal concave surfaces 510 that extend axially or longitudinally therealong. The non-round profile aids in avoiding the rotation of the SI joint surfaces around the long axis of the implanted dowel 500, providing further stabilization of the joint. The dowel body 500a may have a single or multiple concave surfaces 510, producing a generally rectangular cross-sectional shape with two concave surfaces 510, a generally triangular cross-sectional shape with three concave surfaces 510, etc. Instead of concave surfaces 510, dowel body 500a may have one or more longitudinal flat surfaces 104 as shown in FIG. 1A. The flat surfaces 104 and concave surfaces 510 extend along the length of the elongate dowel body 500a at least sufficient to engage the bone of the sacrum and ilium. Flat surfaces 104, concave surfaces 510, and other non-round surface profiles can be combined to provide specific desired cross-sectional profiles as well as a flexural stiffness for dowel 500 that varies depending on the direction of applied force.

The outer geometry of dowel 500 is configured with a reduction in the outer dimension of dowel 500 at step 532, to provide engagement with the surface of the sacrum within the interior of the SI joint sufficient to prevent further movement of dowel 500 through the pre-drilled hole in the sacrum during insertion. This action is enabled by first drilling a smaller hole through the SI joint, sized to allow only the smaller distal portion of dowel 500 to step 532, then drilling a larger hole only through the ilium, sized to allow insertion of the entire dowel 500.

Dowel body 500a is configured with side holes 512 positioned in the central and distal portions of dowel 500 that extend transverse to the length of the body 300a to open to both outer surface 510 and the inner chamber 514. The embodiment shown in FIGS. 15, 16, 17, 18A and 18B shows two rectangular shaped side holes 512 on each of the sides of the dowel body 500a, but other quantities and other shapes of side holes 512 could be used. Side holes 512 are intended to offer the surgeon the option to pack the inner chamber 514 and side holes 512 of dowel 500 with morselized autologous bone, demineralized donor bone product, or bone analogue, with or without bone growth proteins in order to aid new bone growth in general and interlocking bone growth in particular.

Dowel 500 is configured with an inner chamber 514 and proximal hole 507 sized to contain distraction assembly 518 in a non-operative configuration. Distraction assembly 518 consists of an actuator in the form of a central pin 520, having a region with a screw thread 529 located proximal to the medial portion of central pin 520. Threaded sleeve 523 has a screw thread on the internal surface of the sleeve, and is movably attached to central pin 520 proximal to the medial portion of central pin 520 such that the threads of threaded sleeve 523 engages screw thread 529. Extendable anchor members such as paddles 524 are attached to threaded sleeve 523 such that they are allowed to pivot with respect to the longitudinal axis of dowel 500, and positioned within projection holes 526. Projection holes 526 connect outer surface 510 with inner chamber 514. A cam surface is disposed at the medial edge of the holes 526 and is configured to form an upward-angled edge opposite the medial edge cam surface such that longitudinal movement of paddles 524 toward and along the cam surface laterally from the medial location causes paddles 524 to pivot away, and extend outward, from dowel body 500a. Paddles 524 are shown in extended position in FIGS. 15 and 16, and are shown in retracted position in FIG. 17. Extension of paddles 524 is accomplished by rotating central pin 520 in a paddle actuating direction using a drive instrument such as a standard screwdriver designed to engage drive slot 530 in the head of the actuator pin 520. Drive slot 530 can alternatively be configured to accommodate other engagement instruments such as hex wrenches, box wrenches, Torx wrenches, Allen wrenches, or similar designs.

Paddles 524 proximal to the medial portion of dowel 500 are intended to engage the surface of the ilium within the interior of the SI joint once dowel 500 has been positioned within the pre-drilled holes through the SI joint surfaces and paddles 524 have been extended via rotation of central pin 520. Continued rotation of central pin 520 following bone engagement by paddles 524 will urge the joint surfaces apart to impart a distraction force to the SI joint, since step 532 is engaged with the surface of the sacrum within the interior of the SI joint and prevents continued movement of dowel 500 through the pre-drilled hole in the sacrum, with the intent of stabilizing the SI joint by distracting the joint and inducing tension in the ligaments connecting the ilium and sacrum.

Figure 18A:
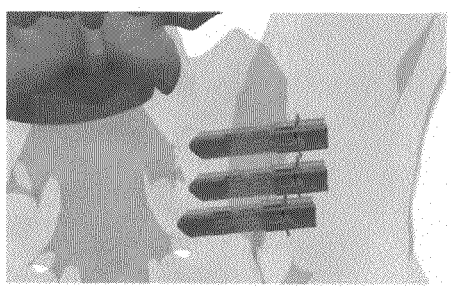
FIGS. 18A and 18B are posterior views of a plurality of dowels according to the embodiment of FIG. 16 implanted within the SI joint showing the paddle members extended.
Figure 18B:
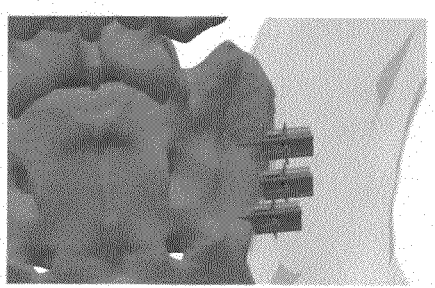

Illustrations showing one example of one embodiment of dowel 500 implanted with paddles in extended positions are shown in FIGS. 18A (sacrum transparent) and 18B (sacrum opaque). While this example shows the use of three dowels 500 with four paddles 524, it should be understood that more or fewer dowels 500 may be implanted depending on individual patient needs and that dowel 500 may be designed with more or fewer paddles.

Dowel 500 and the components of distraction assembly 518 may be made of any biologically inert material with sufficient strength, toughness and other material properties appropriate for their function and use in joint stabilization, including (but not limited to) plastics, metals and ceramics. Suitable plastics include polyether-ether-ketone (PEEK), polyether-ketone-ketone (PEKK) and other related polyaryls, which may be combined with carbon fiber or other fillers to form composites with enhanced material properties. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for dowel 500 and compression assembly 518. Human cadaver donor bone and bone analogues such as coral-derived hydroxyapatite can be used for dowel 500. The outer surface of dowel 500 and at least portions of compression assembly 518 may be modified to enable and/or promote bony tissue in-growth into those surfaces. Surface enhancements may include a roughened surface, or application of a porous (open-pore) version of the underlying substrate material to enable bony in-growth such as porous PEEK or sintered titanium. Other surface enhancements can include application of a non-similar material such as hydroxyapatite.

The next alternative joint fixation connector is in the form of a hollow dowels 600, 601 each having proximal and/or distal zones that expand radially upon insertion of an actuator in the form of a central pin. The expanded zone(s) serve to more fully engage the surrounding bone of the ilium and sacrum for positional fixation of the dowels 600, 601. Two dowels 600 and 601 are described below; the first dowel 600 with only a proximal zone that can expand radially, and a second dowel 601 with the ability to expand radially in both proximal and distal zones. It should be understood that a dowel able to expand radially in only the distal zone is contemplated even though it is not described herein.

Figure 19:
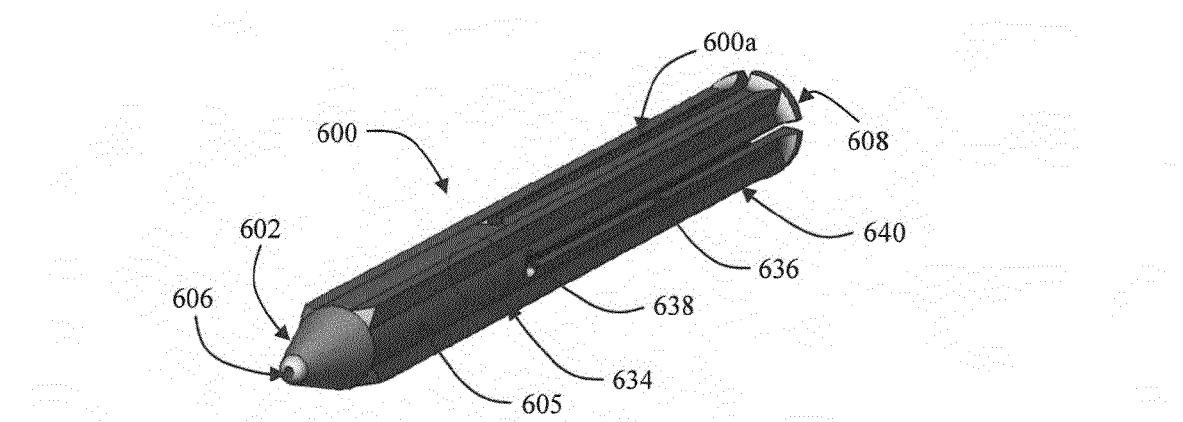
FIG. 19 is a perspective view of an alternate embodiment of a dowel according to the present invention.
Figure 20:
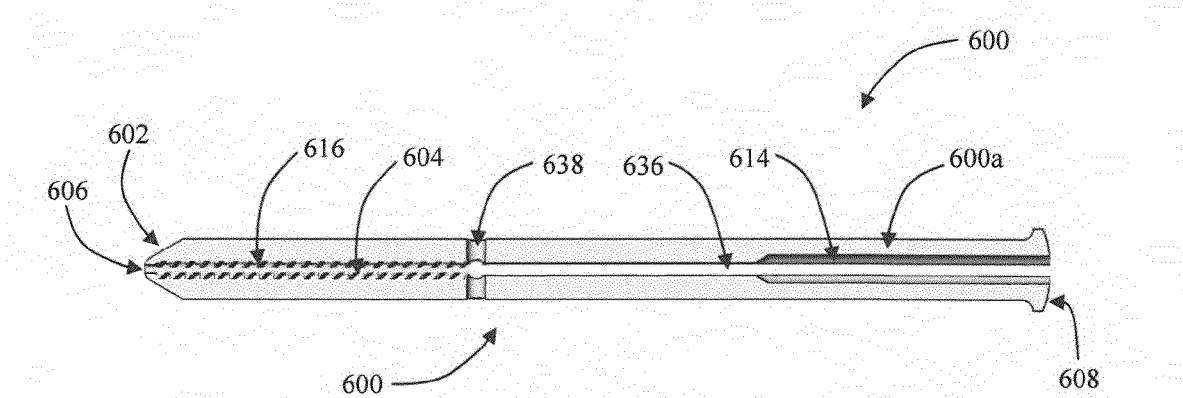
FIG. 20 is a vertical cross-sectional view of the dowel of FIG. 19.
Figure 21:
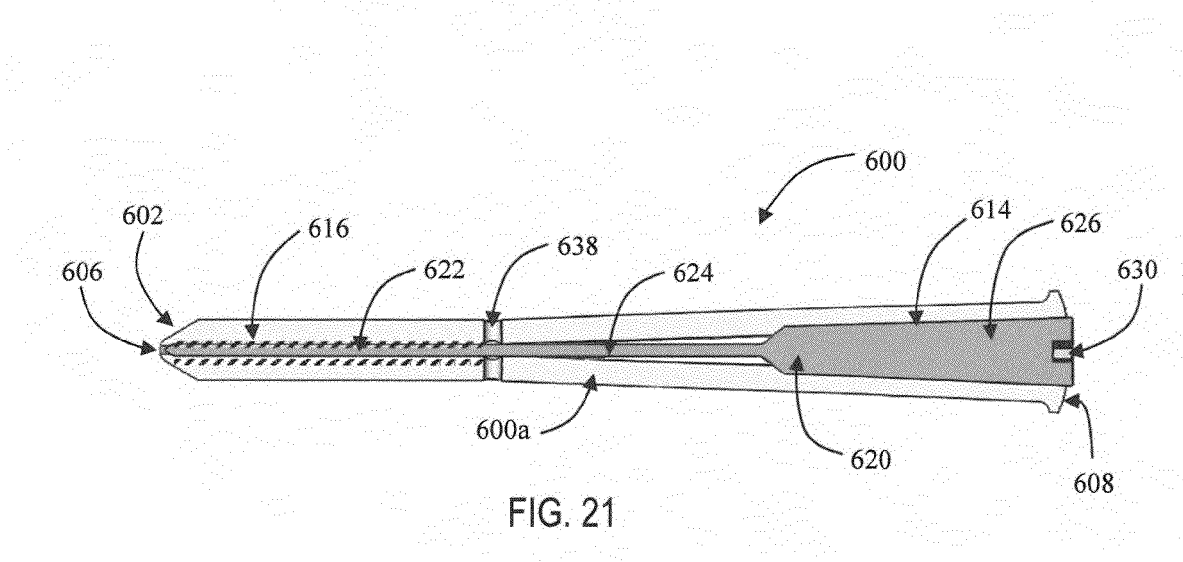
FIG. 21 is a vertical cross-sectional view of the dowel of FIG. 19 with an expansion member inserted within the dowel.

Dowel 600 has an elongate body 600a with no external screw threads and a hollow inner chamber 614 located at the proximal end of dowel body 600a, that is implanted singly or in multiples, and is shown in FIGS. 19-21. Similar to previously described dowels, dowel body 600a has a relatively tapered distal end 602 to assist insertion into a pre-drilled hole through the SI joint surfaces and a relatively blunt proximal end 608 configured for contact with a mallet or other insertion instrument. Dowel body 600a is configured with central bore 604 which extends along the longitudinal axis of dowel 600 from inner chamber 614 through the center of distal end 602. Alternatively, central bore 604 may extend from inner chamber 614 to cannula 606 located at the tip of distal end 602. Cannula 606 would generally have a smaller diameter than central bore 604 to facilitate the use of a guide pin (not shown) intended to aid in placement of dowel 600 into a pre-drilled hole through the SI joint surfaces.

Dowel body 600a has a generally cylindrical primary shape, determined by arcuate surface 605, and has one or more longitudinal ridges 634 extending out radially from and axially along the surface 605 to provide positional stability when implanted. Ridges 634 extend along the length of dowel 600 at least sufficient to engage the bone of the sacrum and ilium. In the embodiment shown, ridges 634 produce a cross-sectional profile for dowel body 600a that is generally square in shape. The use of alternate primary shapes (via alternate surfaces 605) or alternate number or shape of ridges 634 may produce cross-sectional shapes that are generally round, oval, triangular, square, etc. Surface 605 and ridges 634 can be configured and combined to provide specific desired cross-sectional profiles as well as a flexural stiffness for dowel 600 that varies depending on the direction of applied force.

Dowel body 600a is configured with slots 636 that traverse the entire thickness of dowel 600 from inner surface to outer surface 605 thereof. Slots 636 extend along the length of dowel 600 from proximal end 608 to holes 638. The portion of dowel body 600a located between adjacent slots 636 defines expandable arm 640. Holes 638 at the ends of the slots 636 are intended for mechanical stress relief when expandable arm 640 is forced into radial expansion. The position of holes 638 along the length of dowel body 600a determines the length of expandable arms 640, which may extend nearly the entire length of dowel 600. Holes 638 may be arranged to be equally spaced circumferentially about the dowel body 600a as shown in this embodiment, but may also be placed closer or farther apart to create expandable arms 640 with varying widths. The body 600a has internal screw threads 616 formed along the central bore 604 extending from holes 638 to distal end 602 configured to engage the screw threads of central pin 620, and has a major diameter no larger than the diameter of central bore 604 extending from inner chamber 614 to holes 638.

While four slots 636 are incorporated in this embodiment, it should be understood that a single slot 636 is sufficient to allow expansion of dowel 600 and may be used in an alternate embodiment. Likewise, two, three or more than four slots 636 may also be used in an alternate embodiment, and slots in any number need not align with the longitudinal axis in order to provide the expandability feature, e.g., angled or spiral slots.

An actuator in the form of central pin 620 is configured with a distal threaded section 622, unthreaded or smooth section 624 and a proximate tapered or conical-shaped section 626. Threaded section 622 is configured to engage threads 614 along central bore 604, intermediate section 624 is configured to pass freely through central bore 604, and conical-shaped section 626 is configured to slidably engage and cam against the surfaces of inner chamber 614 during insertion of central pin 620 into central bore 604, forcing expandable arms 640 to radially expand. FIG. 21 illustrates this embodiment with central pin 620 fully inserted into central bore 604, resulting in dowel 600 with expandable arms 640 in expanded positions. Central pin 620 is configured with slot drive 630, used for rotating central pin 620 to advance into central bore 604 using a drive instrument such as a standard screwdriver. Slot 630 can alternatively be configured to accommodate other engagement instruments such as hex wrenches, box wrenches, Torx wrenches, Allen wrenches, or similar designs.

Figure 22:
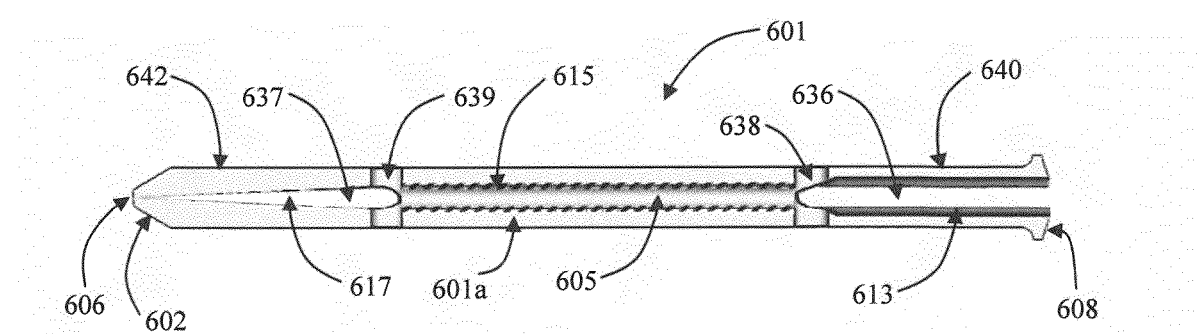
FIG. 22 is a vertical cross-sectional view of an alternate embodiment of a dowel similar to the dowel of FIG. 19.
Figure 23:
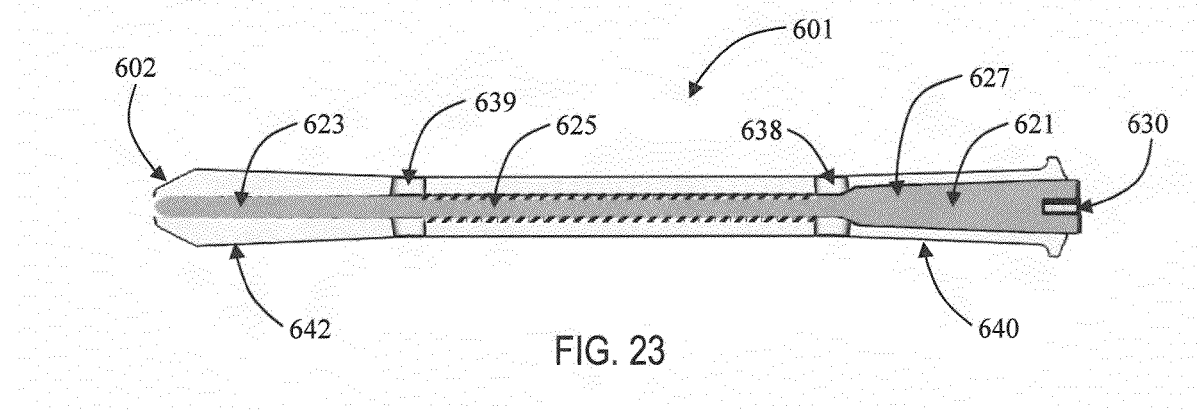
FIG. 23 is a vertical cross-sectional view of the dowel of FIG. 22 with an expansion member inserted within the dowel.

The alternative dowel 601 has an elongate body 601a with slots at both the distal and proximal portions thereof, as shown in FIGS. 22 and 23. Dowel body 601a has generally the same shape, slot and hole configurations as described for dowel body 600a above, including cannula 606 located at the tip of distal end 602, and a relatively blunt proximal end 608 configured for contact with a mallet or other insertion instrument, and slot 630 for central pin rotation. Dowel body 601a has a proximal section having inner chamber 613 and slots 636 extending from proximal end 608 to holes 638, a distal section having inner chamber 617 configured with a tapered or conical shape that tapers to a closed or substantially closed distal end 602 (see FIG. 22) prior to implantation and slots 637 extending from distal end 602 to holes 639, and intermediate section with internal threads 615 formed to extend away central bore 605.

Central pin 621 is configured with a distal unthreaded or smooth section 623, an intermediate threaded section 625 and a proximate tapered or conical-shaped section 627. Threaded section 625 has threads that are configured to engage threads 615 of central bore 605, smooth section 623 is configured to slidably engage the surfaces of inner chamber 617 during insertion of central pin 621 into central bore 605, and conical-shaped section 627 is configured to slidably engage the surfaces of inner chamber 613 during insertion of central pin 621 into central bore 605. The slidable engagement of smooth section 623 with surfaces along inner chamber 617 and conical section 627 with surfaces along inner chamber 613 during insertion of central pin 621 into central bore 605 forces expandable arms 640 and 642 to radially expand, as shown in FIG. 23. Expansion of arms 640 drives the arms to further penetrate into the bone of the ilium, and expansion of arms 642 opens the distal end 602 of body 601a so that the arms 642 are driven to further penetrate into the bone of the sacrum.

Dowel 600 and central pins 620 and 621 may be made of any biologically inert material with sufficient strength, toughness and other material properties appropriate for their function and use in joint stabilization, including (but not limited to) plastics, metals and ceramics. Suitable plastics include polyether-ether-ketone (PEEK), polyether-ketone-ketone (PEKK) and other related polyaryls, which may be combined with carbon fiber or other fillers to form composites with enhanced material properties. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for dowel 600 and central pins 620 and 621. The outer surface of dowel 600 may be modified to enable and/or promote bony tissue in-growth. Surface enhancements may include a roughened surface, or application of a porous (open-pore) version of the underlying substrate material to enable bony in-growth such as porous PEEK or sintered titanium. Other surface enhancements can include application of a non-similar material such as hydroxyapatite.

The following joint fixation device or connector provides positional fixation similar to dowel 600, but does so using a radially expandable sleeve such as in the form deformable mesh which expands radially instead of movable arms. The placement of the mesh along the length of the dowel allows the possibility of compression or distraction of the SI joint and is described in detail below.

Figure 24:
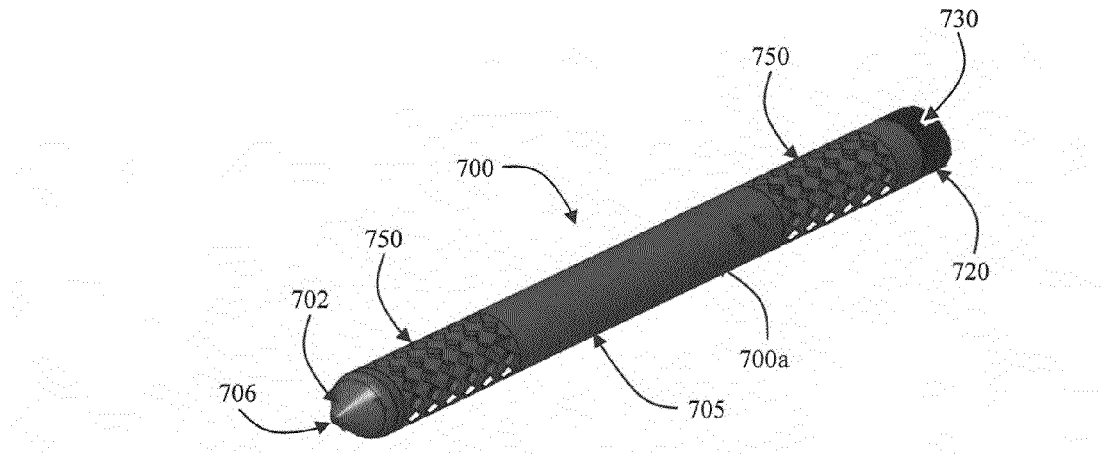
FIG. 24 is a perspective view of an alternate embodiment of a dowel according to the present invention.
Figure 25:
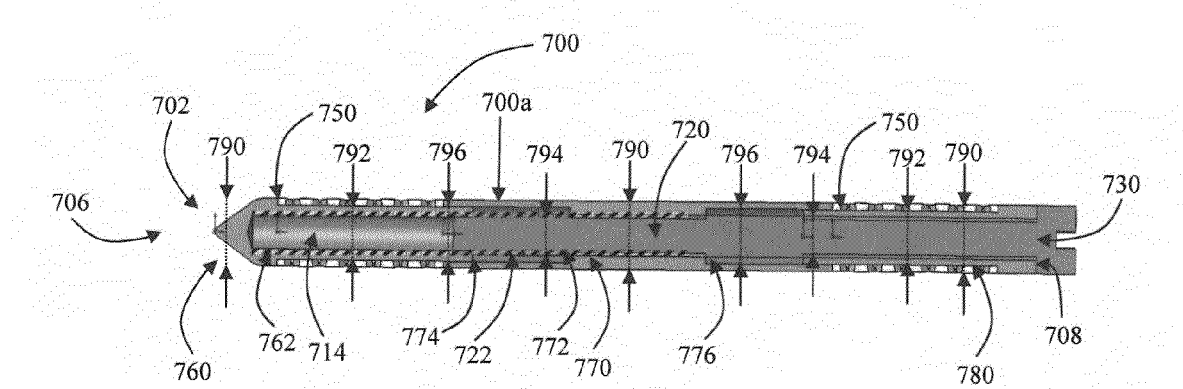
FIGS. 25 and 26 are vertical cross-sectional views of the dowel of FIG. 24 with the radially expandable mesh in unexpanded and expanded configurations.
Figure 26:
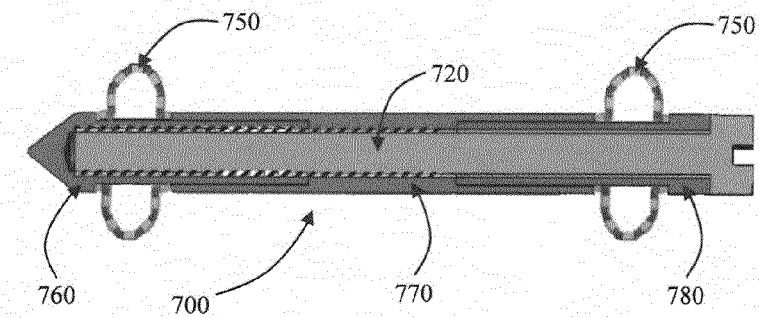

Dowel 700 has no external threads, a hollow inner chamber 514, and can be implanted singly or in multiples, and is shown in FIGS. 24-26. In this device, elongate dowel body 700a is comprised of three tubular members or constructs: distal tube 760, medial tube 770 and proximal tube 780. Distal tube 760 has a relatively tapered distal end 702 to assist insertion into pre-drilled holes through the SI joint surfaces. While not shown in this embodiment, distal tube 760 may be configured with a cannula 706, which is a hole bored generally along the longitudinal axis of distal tube 760 to facilitate the use of a guide pin (also not shown) intended to aid in placement of dowel 700 into a pre-drilled hole through the SI joint surfaces.

The dowel body 700a is shown as having an outer surface 705 that is arcuate, and preferably such that the body surface 705 has a circular cross-sectional configuration. While the circular profile is used to illustrate the concept, it should be understood that at least portions of the profile of dowel 700 could be non-circular, such as an oval, triangular, square, or other combinations of various numbers of flat, concave or convex surfaces. The use of non-circular profiles for dowel body 700a may be useful for a variety of reasons specific to the intended application, such as imparting varied flexural stiffness along the length of dowel 700, increasing contact area with surrounding bone and improving positional stability.

Medial tube 770 has a single outer diameter 790, the major outer diameter of dowel body 700a. Distal tube 760 is configured to have two outer diameters along its length proximal to tapered distal end 702, with an outer surface portion having the distal-most outer diameter 790 and an adjacent outer surface portion having a smaller proximal-most outer diameter 792 to form a step therebetween via a transversely extending outer shoulder surface. Proximal tube 780 is also configured to have two outer diameters along its length, with an outer surface portion having the proximal-most outer diameter 790 and an adjacent outer surface portion having a smaller distal-most outer diameter 792 to form a step therebetween via a transversely extending outer shoulder surface.

Medial tube 770 is configured to have two inner diameters along its length, with an inner medial surface portion having inner diameter 794 and adjacent end surface portions each having a larger inner diameter 796 extending from either end of the medial surface portion of medial tube 770. This provides the medial tube 770 with a pair of transversely inner shoulder surfaces between the smaller diameter medial surface portion and the larger diameter end surface portions. Larger inner diameter 796 of medial tube 770 is sized to provide a slip fit (slidable contact) with the surface portions of distal tube 760 and proximal tube 780 having outer smaller diameter 792. The axial length of the surface portions of distal tube 760 and proximal tube 780 having diameter 792 are sufficient for mounting of deformable mesh 750 in its undeformed—shape as manufactured, on the smaller diameter portions of the tubes 760 and 780 the combination of which defines the relaxed assembled state of dowel 700 as shown in FIGS. 24 and 25.

In this device deformable mesh 750 is tubular in shape as manufactured, and is configured to have an inner diameter to provide a slip fit (slidable contact) with the smaller diameter portions of distal tube 760 and proximal tube 780 having diameter 792, and has the same general outer diameter 790 of medial tube 770. The deformable mesh 750 has an axial length sized so that it is retained on the surface portions of distal tube 760 and proximal tube 780 having diameter 792. More particularly, the distal mesh 750 is retained between distal and intermediate outer shoulder surfaces that extend transverse to smaller diameter surface portion of distal tube 760. Similarly, the proximate mesh 750 is retained between intermediate and proximate outer shoulder surfaces that extend transverse to smaller diameter surfaces portion of proximal tube 780. The medial portion of deformable mesh 750 is configured with holes that provide predictable radial expansion of deformable mesh 750 upon compression of the mesh 750. The holes of deformable mesh 750 may be square in shape as shown in FIG. 24, or may alternatively be rectangular, circular, hexagonal or of any other shape that is able to produce predictable radial expansion. While deformable mesh 750 is tubular in shape in its manufactured state in this embodiment, it should be understood that alternative shapes may be used to match the alternative shapes of dowel 700 described above.

Distal tube 760, medial tube 770 and proximal tube 780, when assembled as shown in FIGS. 24 and 25 to form dowel 700, combine to form inner chamber 714 with sliding zones 774 and 776. The inner surface of distal tube 760 is configured with a screw thread 762. The inner surfaces of medial tube 770 and proximal tube 780 are smooth; with inner diameters 794 sufficient to accommodate unimpeded insertion and rotation of actuator in the form of central pin 720. Siding zones 774 and 776 allow for the longitudinal movement of distal tube 760 and proximal tube 760, respectively, along the longitudinal axis of dowel 700 within medial tube 770.

Central pin 720 is configured for insertion into inner chamber 714 and threaded engagement with distal tube 760 via screw thread 722 of pin 720. Central pin 720 is configured with drive slot 730, used for rotating central pin 720 using a drive instrument such as a standard screwdriver. Drive slot 730 can alternatively be configured to accommodate other engagement instruments such as hex wrenches, box wrenches, Torx wrenches, Allen wrenches, or similar designs. Central pin 720 is configured with a relatively blunt proximal end 708 designed for contact with a mallet or other insertion instrument.

Once in place within the pre-drilled hole through the SI joint, dowel 700 is secured in position by rotating central pin 720 to cause distal tube 760 and proximal tube 780 to slide and be retracted within medial tube 770 due to the engagement of screw thread 762 of distal tube 720 with screw thread 722 of central pin 720, resulting in reduction of the length of dowel 700 and compression of the distal and proximal meshes 750. More particularly, rotation of the threaded pin actuator 720 causes the small diameter portion of the distal tube 760 to be drawn into the medial tube 770 along slide zone 774 until its end abuts the inner distal shoulder surface of the tube 770. Rotation of the threaded pin actuator 720 also causes enlarged head of the pin actuator 720 to push the small diameter portion of the proximal tube 780 into the medial tube 770 along zone 776 until its end abuts inner proximal shoulder surface of the tube 770. As dowel 700 is shortened in axial length, deformable meshes 750 located at the distal and proximal portions of dowel 700 are placed under compressive forces between the corresponding outer shoulder surfaces and relieve these forces through radial expansion. Deformable mesh 750 which has expanded radially will frictionally contact the surrounding ilium and sacrum bones of the SI joint, resulting in fixation of dowel 700 within the SI joint. An illustration of the present embodiment in completely shortened, retracted, or compressed form, with complete expansion of deformable mesh 750 and taking up of sliding zones 774 and 776 by the small diameter portions of tubes 760 and 780 is shown in FIG. 26.

Other embodiments of dowel 700 may include configurations where sliding zones 774 and 776 are not completely taken up upon complete retraction or compression. Alternate embodiments may also include placement of mesh 750 in distal and proximal regions of dowel 700 that provide for the engagement of the exterior surfaces of the ilium and sacrum of the SI joint to provide compression of the SI joint following expansion of mesh 750, or placement of mesh 750 in relatively medial locations of dowel 700 that provide for the engagement of the interior surfaces of the ilium and sacrum of the SI joint to provide distraction of the SI joint following expansion of mesh 750, with compression or distraction capable of providing stability to the SI joint. Other alternate embodiments may include the use of only one mesh 750, or more than the two locations of mesh 750 that have been described herein.

The components comprising dowel 700 may be made of any biologically inert material with sufficient strength, toughness and other material properties appropriate for their function and use in joint stabilization, including (but not limited to) plastics, metals and ceramics. Suitable plastics include polyether-ether-ketone (PEEK), polyether-ketone-ketone (PEKK) and other related polyaryls, which may be combined with carbon fiber or other fillers to form composites with enhanced material properties. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for distal tube 760, medial tube 770, proximal tube 780, mesh 750 and central pin 720. Human cadaver donor bone and bone analogues such as coral-derived hydroxyapatite can also be used for dowel 700. At least portions of the outer surfaces of distal tube 760, medial tube 770, proximal tube 780 and mesh 750 may be modified to enable and/or promote bony tissue in-growth into those surfaces. Surface enhancements may include a roughened surface, or application of a porous (open-pore) version of the underlying substrate material to enable bony in-growth such as porous PEEK or sintered titanium. Other surface enhancements can include application of a non-similar material such as hydroxyapatite.

The following joint fixation device or connector provides positional fixation once implanted, using two screw threaded sleeves to engage the surrounding bone of the SI joint. This device can be implanted in fully-assembled form or be assembled in situ, wholly or in part. Variations of particular aspects of this device can induce compression or distraction of the SI joint as desired by the surgeon for joint stabilization prior to fusion.

Figure 27:
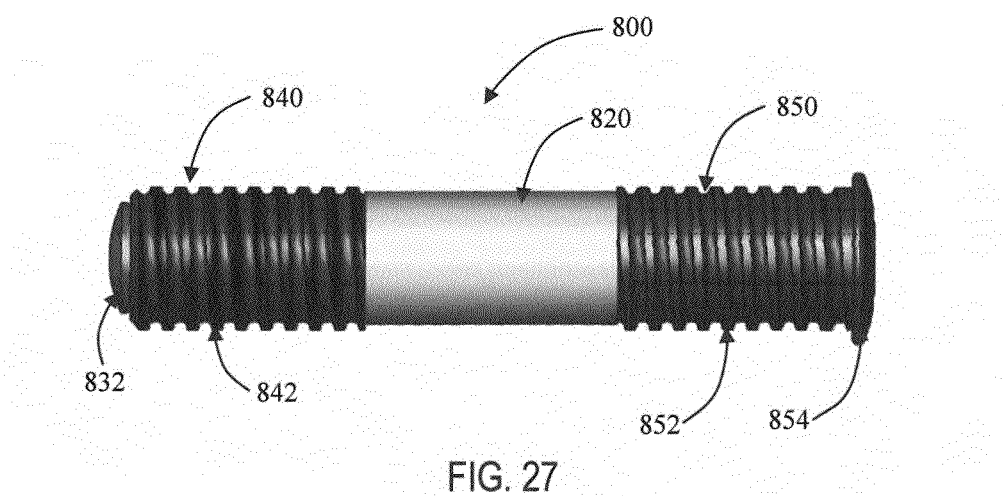
FIG. 27 is a side elevation view of an alternate embodiment of a dowel according to the present invention.
Figure 28:
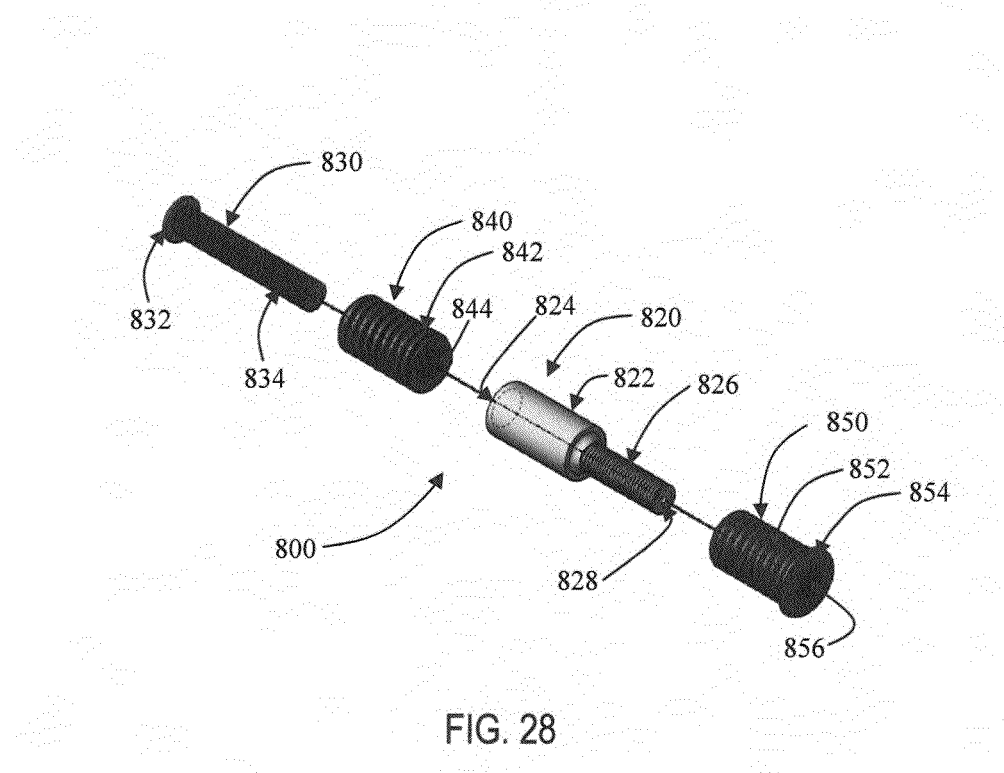
FIG. 28 is an exploded perspective view of the dowel of FIG. 27.

The device can be in the form of a dowel 800 that is implanted singly or in multiples, and is shown in FIGS. 27 and 28. Dowel 800 is comprised of multiple components or members including proximal pin 820, distal pin 830, distal sleeve 840 and proximal sleeve 850. In alternate embodiments, dowel 800 may also incorporate additional components as needed to facilitate insertion of the components and relative rotation of the threaded components as described below.

Distal pin 830 is configured similar to a machine bolt, with a pin head 832 and a pin threaded shank portion 834. Pin head 832 has an outer diameter less than the diameter of the pre-drilled hole through the SI joint, but larger than the inner diameter of distal sleeve 840. Pin threaded portion 834 is configured to engage the inner screw thread 844 of distal sleeve 840 and threaded hole or cylindrical cavity 824 of proximal pin 820.

Proximal pin 820 is generally cylindrical in shape and can be configured with a smooth portion 822 having a diameter larger than the inner diameter of sleeve 850 but no greater than the minor diameter of thread 852 of sleeve 850. The cylindrical cavity within smooth portion 822 is open to the distal end of proximal pin 820, and is threaded to be configured to engage with threaded portion 834 of distal pin 830. Proximal pin 820 has a screw threaded portion 826 configured to engage inner thread 856 of proximal sleeve 850. Proximal end 828 of threaded portion 826 of proximal pin 820 may be configured with a slot used for rotating proximal pin 820 during implantation using an instrument such as a standard screwdriver, or can alternatively be configured to accommodate other engagement instruments such as hex wrenches, box wrenches, Torx wrenches, Allen wrenches, or similar designs.

Distal sleeve 840 is configured with outer thread 842 along its outer surface which is intended to engage the bone of the sacrum in the SI joint, and inner thread 844 along its inner surface which is configured to engage threaded portion 834 of distal pin 830.

Proximal sleeve 850 is configured with outer thread 852 along its outer surface which is intended to engage the bone of the ilium in the SI joint, inner thread 856 along its inner surface which is configured to engage threaded portion 826 of proximal pin 820, and radially enlarged end flange 854 which is intended to avoid over-insertion of dowel 800 by contacting the outer surface of the ilium of the SI joint. Flange 854 may have drive slots, holes, projections or other such features along its radial or proximal surfaces configured for engagement of a drive instrument to allow for rotation of proximal sleeve 850 relative to proximal pin 820.

Dowel 800 can be completely assembled as shown in FIG. 27 and threaded into a pre-drilled hole through the SI joint. Alternatively, distal pin 830, distal sleeve 840 and proximal pin 820 can be assembled prior to implantation and threaded into a pre-drilled hole through the SI joint, with proximal sleeve 850 threaded onto distal pin 830 to complete the implantation of dowel 800. This two-step in situ assembly may allow for a more customized fit of dowel 800 to an individual patient's anatomical requirements. Furthermore, dowel 800 may be entirely assembled in situ, first by insertion of distal pin 830 through a pre-drilled hole through the SI joint, followed by threaded assembly of distal sleeve 840 over distal pin 830 and engaging the bone of the sacrum, with subsequent threaded assembly of proximal pin 820 over the remaining portion of distal pin 830, and finally with threaded assembly of proximal sleeve 850 over proximal pin 820 and engaging the bone of the ilium.

Sleeve 840 can have a smaller nominal diameter than proximal pin 820, necessitating a hole through the sacrum that is smaller than that through the ilium. Sleeve 840 can have a diameter such that the distal surface of proximal pin 820 engages with the surface of the sacrum within the interior of the SI joint sufficient to avoid further movement of dowel 800 through the pre-drilled hole in the sacrum during insertion.

Proximal pin 820 can be configured with a relatively short axial length of smooth portion 822, such that continued rotation of proximal sleeve 850 relative to proximal pin 820 following engagement of flange 854 with the outer surface of the ilium causes the inner surfaces of the sacrum and ilium of the SI joint to compress to increase the stability of the SI joint prior to fusion.

The components comprising dowel 800 may be made of any biologically inert material with sufficient strength, toughness and other material properties appropriate for their function and use in joint stabilization, including (but not limited to) plastics, metals and ceramics. Suitable plastics include polyether-ether-ketone (PEEK), polyether-ketone-ketone (PEKK) and other related polyaryls, which may be combined with carbon fiber or other fillers to form composites with enhanced material properties. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for dowel 800. In particular, the design of distal pin 830 and proximal pin 820 allows for dowel 800 to be built with an overall stiffness ranging from extremely stiff, through use of a metal such as a titanium alloy, to a stiffness similar to that of bone through use of PEEK. Human cadaver donor bone and bone analogues such as coral-derived hydroxyapatite can also be used for distal sleeve 840 and proximal sleeve 850 of dowel 800. At least portions of the outer surfaces of distal sleeve 840 and proximal sleeve 850 may be modified to enable and/or promote bony tissue in-growth into those surfaces. Surface enhancements may include a roughened surface, or application of a porous (open-pore) version of the underlying substrate material to enable bony in-growth such as porous PEEK. Other surface enhancements can include application of a non-similar material such as hydroxyapatite.

The following joint fixation device or connector provides positional fixation once implanted, using two screw threaded sleeves which expand to further engage the surrounding bone of the SI joint. This device can be implanted in fully-assembled form or be assembled in situ. The threaded sleeves can be screwed into place during implantation, with the threads engaging the surrounding bone, prior to expansion of the sleeves, or the diameter of the pre-drilled hole through the SI joint can be such that the sleeves do not engage the surrounding bone until expansion of the sleeves.

Figure 29:
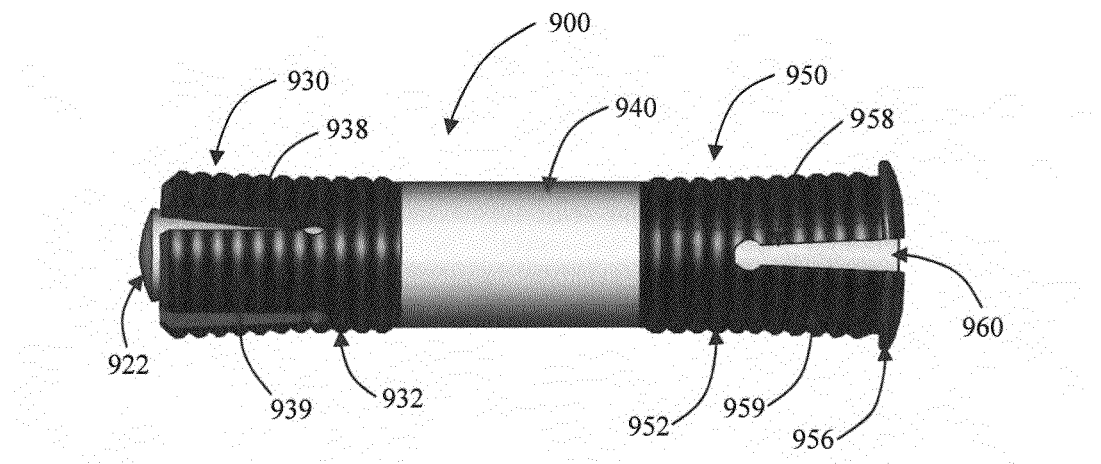
FIG. 29 is a side elevation view of an alternate embodiment of a dowel according to the present invention.
Figure 30:
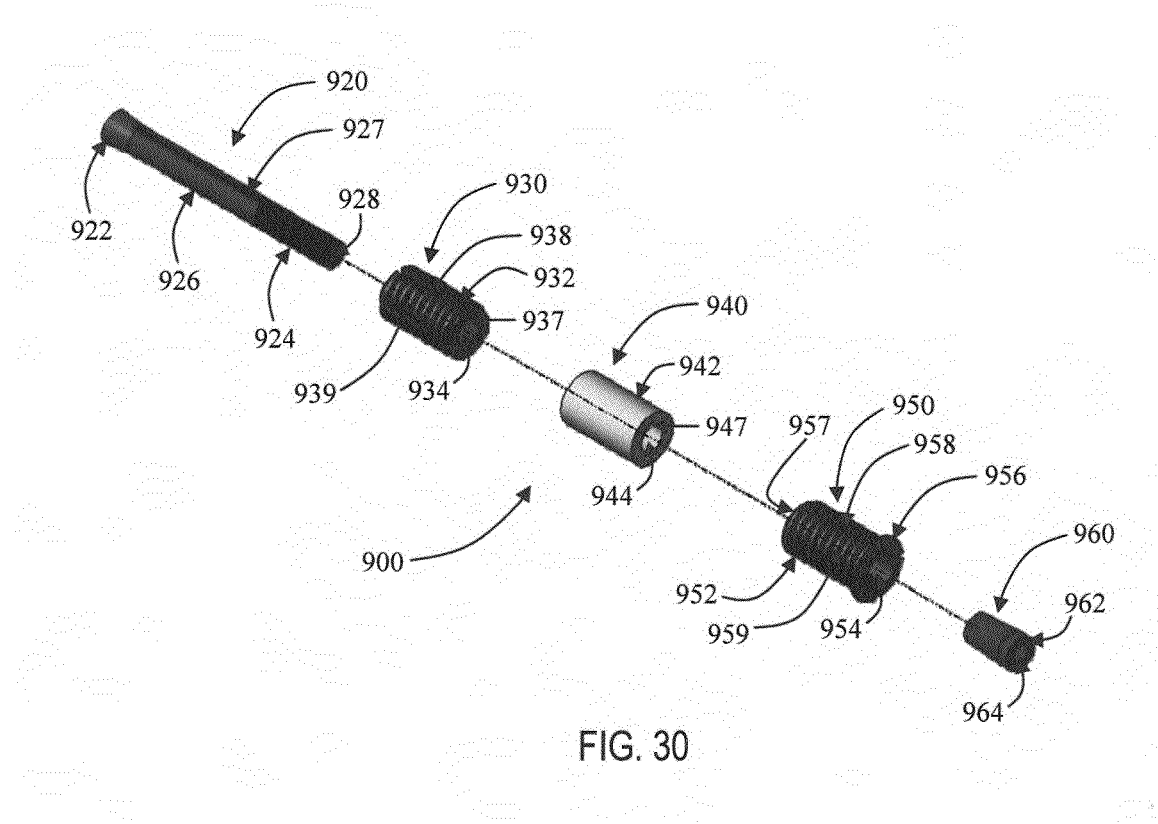
FIG. 30 is an exploded perspective view of the dowel of FIG. 29.

This device can be in the form of a dowel 900 that is implanted singly or in multiples, and is shown in FIGS. 29 and 30. Dowel 900 is comprised of multiple components or members, including central pin 920, distal sleeve 930, central sleeve 940, proximal sleeve 950 and tapered tube 960. In alternate embodiments, dowel 900 may also incorporate additional components as needed to facilitate insertion of the components and relative rotation of the threaded components as described below.

Central pin 920 is configured with flared distal tip end 922, smooth portion 926, rail 927 and screw threaded portion 924 configured to engage inner screw thread 964 of tapered tube 960. The flared configuration of distal tip 922 is such that it is operable to expand arms 939 of distal sleeve 930 during implantation of dowel 900. Rail 927 projects from the surface of central pin 920, extends from distal tip 922 to threaded portion 924 and is configured to slidably engage corresponding slots in the three sleeves to avoid rotation of central pin 920 during rotation of tapered tube 960 during final assembly and expansion of the distal and proximal sleeves. Distal tip 922 has an outer diameter less than the diameter of the pre-drilled hole through the SI joint, but larger than the inner diameter of distal sleeve 930. Central pin 920 may be configured with drive slot 928 (indicated but not shown in FIG. 30), used for rotating central pin 920 using an instrument such as a standard screwdriver. Drive slot 928 can alternatively be configured to accommodate other engagement instruments such as hex wrenches, box wrenches, Torx wrenches, Allen wrenches, or similar designs.

Distal sleeve 930 is configured with an outer surface having screw thread 932 along its outer surface which is intended to engage the bone of the ilium in the SI joint, a relatively smooth inner surface 934 having a channel 937, and through slots 938. For embodiments of dowel 900 where the bone-contacting sleeves are not intended to be screwed into the surrounding surfaces prior to expansion of the sleeves, surface features to enhance friction other than screw threads may be used, such as circumferential, longitudinal or angled ridges; cross-hatching; roughened surfaces, etc. Slots 938 extend through the entire sleeve wall, originate at the distal end, project along the longitudinal axis and terminate along the wall or body of sleeve 930 before reaching the proximate end thereof. Four slots are incorporated in this embodiment, defining arms 939 which are able to expand radially away from the central axis of sleeve 930. It should be understood that a single slot 938 is sufficient to allow expansion of distal sleeve 930 and may be used in an alternate embodiment. Likewise, two, three or more than four slots 938 may also be used in an alternate embodiment, and slots in any number need not align with the longitudinal axis in order to provide the expandability feature, e.g., angled or spiral slots. Slots 938 may terminate at a hole passing through the wall of sleeve 930 which acts as a mechanical stress relief during expansion. Channel 937 is configured to slidably engage rail 927 of central pin 920.

Central sleeve 940 has an outer diameter larger than the inner diameter of both sleeve 930 and sleeve 950 but no greater than the minor diameter of thread 932 of sleeve 930 and sleeve 952 of sleeve 950. The inner diameter of central sleeve 940 is sized to allow central sleeve 940 to move freely over central pin 920 during assembly. The inner surface of central sleeve 940 has an inner channel 947 configured to slidably engage rail 927 of central pin 920.

Proximal sleeve 950 is configured with an outer surface having screw thread 952 along its outer surface which is intended to engage the bone of the ilium in the SI joint, a relatively smooth inner surface 954, flange 956, inner channel 957 (indicated but not shown in FIG. 30) and slots 958. For embodiments of dowel 900 where the bone-contacting sleeves are not intended to be screwed into the surrounding surfaces prior to expansion of the sleeves, surface features of proximal sleeve 950 to enhance friction other than screw threads 952 may be used, such as circumferential, longitudinal or angled ridges; cross-hatching; roughened surfaces, etc. Slots 958 extend through the entire sleeve wall, originate at the proximal surface of flange 956, project along the longitudinal axis and terminate along the wall or body of sleeve 950 before reaching the distal end thereof. Four slots are incorporated in this embodiment, defining arms 959 which are able to expand radially away from the central axis of sleeve 950. As with distal sleeve 930, it should be understood that a single slot 958 is sufficient to allow expansion of distal sleeve 950 and may be used in an alternate embodiment. Likewise, two, three or more than four slots 958 may also be used in an alternate embodiment, and slots in any number need not align with the longitudinal axis in order to provide the expandability feature, e.g., angled or spiral slots. Slots 950 may terminate at a hole passing through the wall of sleeve 950 which acts as a mechanical stress relief during expansion. Flange 956 is intended to avoid over-insertion of dowel 900 by contacting the outer surface of the ilium of the SI joint. Flange 956 may have drive slots, holes, projections or other such features along its radial or proximal surfaces configured for engagement of an instrument for holding proximal sleeve 950 in place while rotating tapered tube 960.

Tapered tube 960 has a screw threaded inner surface 964 configured to engage threaded portion 924 of central pin 920, and a relatively smooth outer surface with a diameter that increases from the distal end to the proximal end of tapered tube 960. The tapered configuration of the tube 960 is such that it is operable to expand arms 959 of proximal sleeve 950 during implantation of dowel 900 as shown in FIG. 29. The proximal surface of tapered tube 960 may have drive slots, holes, projections or other such features along its radial or proximal surfaces configured for engagement of a rotary drive instrument to allow for rotation of tapered tube 960 relative to proximal pin 920.

Dowel 900 can be completely assembled, but without complete rotation of tapered tube 960 and sleeve arm expansion, and inserted and screwed into a pre-drilled hole through the SI joint using slot 928 of central pin 920. Tapered tube 960 is screwed into final position, radially expanding arms 939 of distal sleeve 930 and arms 959 of proximal sleeve 950 by compression of the tapered portions of central pin 920 and tapered tube 960 into their corresponding sleeves, as shown in FIG. 29. Alternatively, the pre-drilled hole through the SI joint may be large enough to avoid engagement of dowel 900 with the surrounding bone prior to expansion of arms 939 and 959, allowing dowel 900 to be positioned without needing to screw it in, followed by screwing tapered tube 960 into final position to radially expand arms 939 and 959 to engage the surrounding bone of the SI joint.

Alternatively, dowel 900 may be entirely assembled in situ, first by insertion of central pin 920 through a pre-drilled hole through the SI joint having a diameter sufficiently large to enable placement of each sleeve without rotation, followed by insertion of distal sleeve 930, central sleeve 940, and proximal sleeve 950 through the hole in the SI joint and over central pin 920 and alignment of channels 937, 947 and 957 with rail 927. Once in place, tapered tube 960 is screwed into final position to radially expand arms 939 and 959 to engage the surrounding bone of the SI joint.

Distal sleeve 930 can have a smaller diameter than central sleeve 940, necessitating a hole through the sacrum that is smaller than that through the ilium. Distal sleeve 930 can have a diameter such that the distal surface of central sleeve 940 engages with the surface of the sacrum within the interior of the SI joint sufficient to prevent further movement of dowel 900 through the pre-drilled hole in the sacrum for added security of placement during insertion.

The components comprising dowel 900 may be made of any biologically inert material with sufficient strength, toughness and other material properties appropriate for their function and use in joint stabilization, including (but not limited to) plastics, metals and ceramics. Suitable plastics include polyether-ether-ketone (PEEK), polyether-ketone-ketone (PEKK) and other related polyaryls, which may be combined with carbon fiber or other fillers to form composites with enhanced material properties. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for dowel 900. In particular, the design of central pin 920 and central sleeve 930 allows for dowel 900 to be built with an overall stiffness ranging from extremely stiff, through use of a metal such as a titanium alloy, to a stiffness similar to that of bone through use of PEEK. Human cadaver donor bone and bone analogues such as coral-derived hydroxyapatite can also be used for distal sleeve 930 and proximal sleeve 950 of dowel 900. At least portions of the outer surfaces of distal sleeve 930 and proximal sleeve 950 may be modified to enable and/or promote bony tissue in-growth into those surfaces. Surface enhancements may include a roughened surface, or application of a porous (open-pore) version of the underlying substrate material to enable bony in-growth such as porous PEEK. Other surface enhancements can include application of a non-similar material such as hydroxyapatite.

The following joint fixation device or connector is comprised of two threaded bone-contacting sleeves and an expansion member, which when fully assembled in situ engages and expands into the bone of a synovial joint, such as the ilium and sacrum, to secure the fixation device in place and thereby keep the device from retracting from the bone. This concept also provides the capability for SI joint compression or distraction while simultaneously stabilizing the joint. Although this embodiment is described with reference to the SI joint, it is understood that this embodiment may have applicability in other synovial joints.

Figure 31:
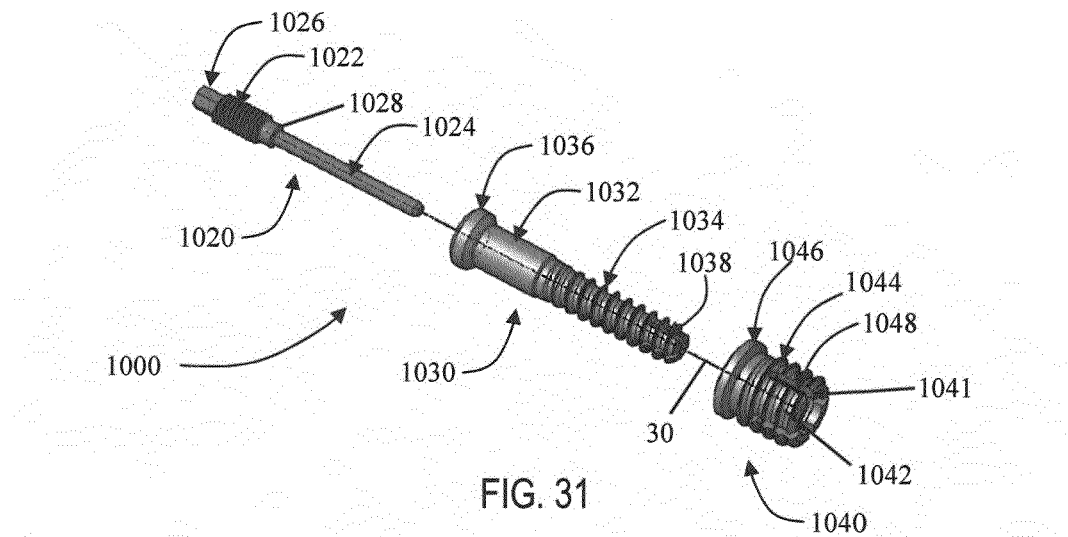
FIG. 31 is an exploded perspective view of the fixation device of FIG. 32.
Figure 32:
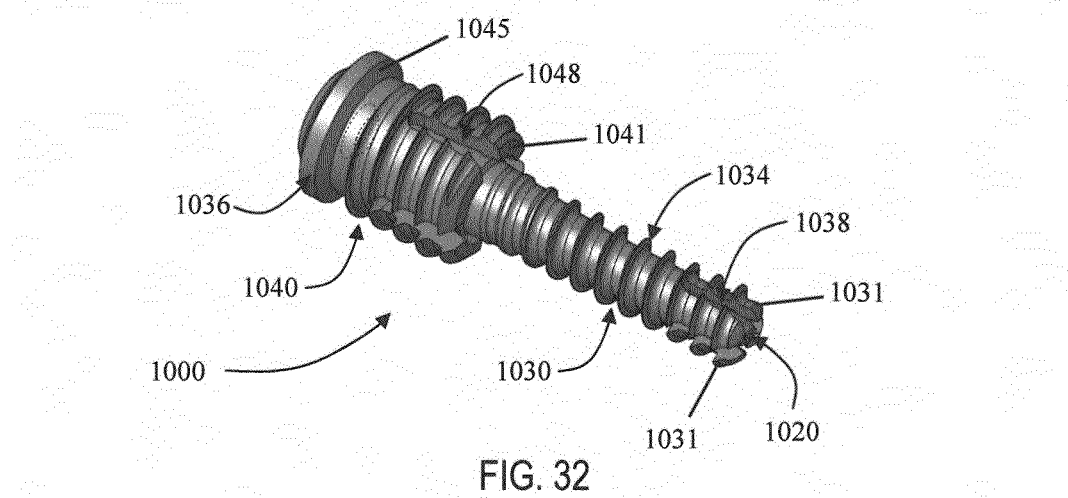
FIG. 32 is a perspective view of an alternate embodiment of a fixation device according to the present invention.
Figure 33:
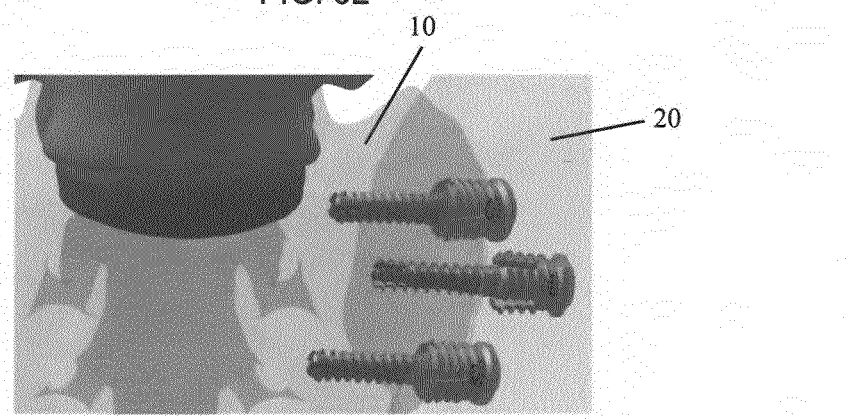
FIG. 33 is an anterior view of a plurality of fixation devices as shown in FIG. 32 implanted within the SI joint.
Figure 34:
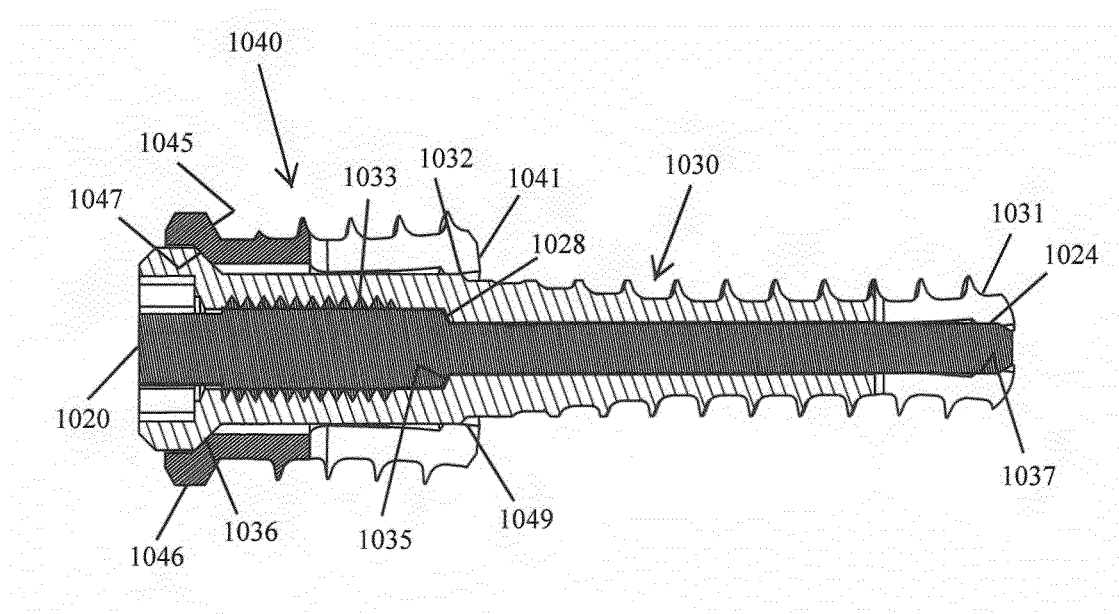
FIG. 34 is a vertical cross sectional view of the fixation device of FIG. 32.

This device can be in the form of a multipiece fastener or dowel 1000 that is implanted singly or in multiples, and is shown in FIGS. 31, 32, 33, and 34. As shown in FIGS. 31 and 32, dowel 1000 is comprised of an expansion member in the form of central pin 1020, a first expandable fastener in the form of outer sleeve 1040, and a second expandable fastener in the form of inner sleeve 1030. Advantageously, the inner sleeve 1030 is configured to both fix the adjacent first and second bones of synovial joint in conjunction with the outer sleeve 1040, as well as expand an expandable portion of the outer sleeve 1040 to firmly fix the outer sleeve to the first bone. The central pin is preferably configured to expand an expandable portion of the inner sleeve 1030 to firmly fix the inner sleeve to the second bone of the synovial joint. A longitudinal cross-sectional view of the assembled dowel is shown in FIG. 34.

Outer sleeve 1040 is configured with radially enlarged proximal annular end flange 1046, having an outer diameter that is greater than the pre-drilled hole in the ilium sufficient to allow abutment surface 1045 of outer sleeve 1040 to seat against the outer surface of the ilium of the SI joint to avoid over-insertion during implantation. Outer sleeve 1040 includes an outer bone engaging surface including a helical screw threaded portion 1044 that is configured to be inserted in the bone material of the ilium 20 to secure the position of outer sleeve 1040. Outer sleeve 1040 has at least one slot 1048 positioned to extend axially along threaded portion 1044 extending to the distal end of outer sleeve 1040, to provide at least one radially expandable portion to allow at least part of threaded portion 1044 of outer sleeve 1040 to expand radially outwardly. The embodiment shown in FIGS. 31 and 32 has four slots 1048, creating four arms 1042 that are able to expand radially, although it should be understood that any number of slots may be used and they need not align with the longitudinal axis in order to provide the expandability feature, e.g., angled or spiral slots. The inner annular surface of outer sleeve 1040 defines a longitudinally extending passage that is relatively smooth, and has a diameter that decreases from the proximal portion of outer sleeve 1040 to the distal portion 1049 of outer sleeve 1040, creating an interference fit with smooth annular proximal portion 1032 of inner sleeve 1030 sufficient to provide for subsequent radial expansion of the threaded portion 1044 upon full insertion of inner sleeve 1030 within outer sleeve 1040. The outer sleeve 1040 preferably includes a drive structure, such as a hex head, at the distal end for engaging with a rotary driving tool, such as a screw driver, for driving the outer sleeve into the ilium.

Inner sleeve 1030 is configured with a radially enlarged proximal annular end flange 1036, having an outer diameter that is greater than the inner diameter of outer sleeve 1040 sufficient to allow the flange 1036 of the inner sleeve 1030 to seat against an interior shoulder abutment surface 1047 of flange 1046 of outer sleeve 1040. The inner sleeve 1030 is axially longer than the outer sleeve 1040 and has an outer surface with a smooth unthreaded shaft portion 1032 located proximally for engaging with the interior surface of the outer sleeve 1040 as shown, and helical screw threaded portion 1034 is located distally to extend beyond the distal end of the outer sleeve 1040 when the inner sleeve 1030 is seated therein (FIG. 32) and is configured to engage the bone of the sacrum 10 to secure the position of inner sleeve 1030 and the entire assembled dowel 1000. The screw threaded shaft portion 1034 is preferably tapered radially outward in a distal to proximal direction. Inner sleeve 1030 has at least one slot 1038 positioned to extend axially along threaded portion 1034 to the distal end of inner sleeve 1030, providing a radially expandable portion of the threaded portion of inner sleeve 1030 configured to expand in diameter. The embodiment shown in FIGS. 31 and 32 has four slots 1038, creating four arms 1031 that are configured to radially expand, although it should be understood that any number of slots may be used, and they need not align with the longitudinal axis in order to provide the expandability feature, e.g., angled or spiral slots.

The interior surface of inner sleeve 1030 defines a longitudinally extending passage having a relatively smooth annular distal portion and is internally threaded along a screw threaded proximal portion 1033 configured to engage the external screw threads 1022 of central pin 1020. As shown in FIG. 34, the inner surface of the inner sleeve 1030 includes an abutment surface 1035 extending transverse to the longitudinal axis 30 of the inner sleeve 1030 for engaging with a corresponding abutment surface 1028 of central pin 1020 to provide a limit on how far the central pin may be inserted into the inner sleeve. The diameter of the inner surface of inner sleeve 1030 decreases from the proximal portion of inner sleeve 1030 to the distal portion 1037 of inner sleeve 1030, creating an interference fit with smooth portion 1024 of central pin 1020 sufficient to provide for subsequent radial expansion of the threaded portion 1034 upon full insertion of central pin 1020 within inner sleeve 1030.

Central pin 1020 is configured with hex-shaped pin head 1026, screw threaded proximal portion 1022 and relatively smooth annular distal portion 1024. Pin head 1026 is intended to be engaged by a rotary drive instrument following implantation of outer sleeve 1040, inner sleeve 1030, and insertion of central pin 1020 through inner sleeve 1030. In alternative embodiments, pin head 1026 may have more or less than six flat surfaces, creating other than a hex shape, or have shaped depressions such as a slot, square hole, hex hole, etc. or other internal and/or external configurations known to those skilled in the art that are able to transmit rotational movement from an instrument to central pin 1020. Threaded proximal portion 1022 is configured to threadingly engage the threaded portion 1033 of the internal surface of inner sleeve 1030.

The SI joint is generally prepared for implantation of dowel 1000 by drilling a first recess sized to accommodate outer sleeve 1040 only through the ilium bone 20 of the SI joint. Next, a second recess is formed in the sacrum bone 10 of the SI joint, sized to accommodate a portion of the inner sleeve 1030 and centered on the first recess. The order in which the recesses are drilled may be reversed, or the recesses may be formed simultaneously. Alternatively, the dowel may include self-tapping threads such that forming recesses in the bone prior to insertion of the dowel is unnecessary. Dowel 1000 is generally implanted by first screwing outer sleeve 1040 into the drilled hole through the ilium of the SI joint until the abutment surface 1045 of flange 1046 is seated against the ilium. Inner sleeve 1030 is then inserted through outer sleeve 1040 and screwed into the drilled hole through the sacrum of the SI joint until flange 1036 is seated against the interior abutment surface 1047 of flange 1046. Passage of smooth portion 1032 of inner sleeve 1030 through threaded portion 1044 of outer sleeve 1040 causes the arms 1042 at the distal portion of outer sleeve 1040 to radially expand and further tightly engage the bone of the ilium to fix the outer sleeve thereto. Central pin 1020 is then inserted through inner sleeve 1030 and screwed into inner sleeve 1030 until central pin 1020 is fully seated against inner sleeve 1030. Passage of smooth portion 1024 of central pin 1020 through threaded portion 1034 of inner sleeve 1030 causes the arms 1031 at the distal portion of inner sleeve 1030 to radially expand and further tightly engage the bone of the sacrum to fix the inner sleeve thereto. FIG. 32 is an illustration of dowel 1000 following complete implantation and in situ assembly.

The overall length of outer sleeve 1040 can be varied during manufacture to produce a dowel 1000 that provides either compression or distraction of the SI joint. An outer sleeve 1040 with a short overall length, which limits protrusion of the distal end of the sleeve into the interior of the SI joint, will work in conjunction with inner sleeve 1030 as the inner sleeve 1030 is threaded into the sacrum 10 to pull the sacrum towards the ilium of the SI joint, stabilizing the joint through compression. Alternatively, outer sleeve 1040 can be configured with an overall length that protrudes through the ilium bone 20 and across the SI joint to abuttingly contact the joint surface of the sacrum 10 with an abutment surface 1041 at the distal end of the outer sleeve 1040. Abutment surface 1041 extends transversely to the longitudinal axis 30 such that the outer sleeve 1040 will abut the surface of the sacrum 10 and not protrude into the sacrum. Preferably, the threaded outer surface 1044 of the outer sleeve 1040 is configured to keep the outer sleeve from self-tapping into the sacrum. Once the abutment surface 1040 contacts the sacrum, further insertion of the outer sleeve will apply force to the sacrum and begin to push the ilium away from the sacrum, distracting the joint and inducing tension in the ligaments connecting the ilium and sacrum. Implantation of inner sleeve 1030 and central pin 1020 as described above provides further fixation and stabilization of the distracted joint. Alternatively, implantation of outer sleeve 1040 alone may supply sufficient fixation and stabilization and avoid the need for implantation of the remaining components described above.

Illustrations showing one example of one embodiment of dowel 1000 implanted is shown in FIG. 33. While this example shows the use of three dowels 1000, it should be understood that more or fewer dowels 1000 may be implanted depending on individual patient needs.

The components comprising dowel 1000 may be made of any biologically inert material with sufficient strength, toughness and other material properties appropriate for their function and use in joint stabilization, including (but not limited to) plastics, metals and ceramics. Suitable plastics include polyether-ether-ketone (PEEK), polyether-ketone-ketone (PEKK) and other related polyaryls, which may be combined with carbon fiber or other fillers to form composites with enhanced material properties. Suitable metals include titanium and titanium alloys such as Ti6Al4V and Ti6Al7Nb (commonly used in medical device implants) and various stainless steel formulations. Combinations of the materials listed herein can be used to produce mechanical properties most desired for central pin 1020, inner sleeve 1030 and outer sleeve 1040. Human cadaver donor bone and bone analogues such as coral-derived hydroxyapatite can also be used for inner sleeve 1030 and outer sleeve 1040. At least portions of the outer surfaces of inner sleeve 1030 and outer sleeve 1040 may be modified to enable and/or promote bony tissue ingrowth into those surfaces. Surface enhancements may include a roughened surface, or application of a porous (open-pore) version of the underlying substrate material to enable bony in-growth such as porous PEEK or sintered titanium. Other surface enhancements can include application of a non-similar material such as hydroxyapatite.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A multipiece fastener for stabilizing a synovial joint, comprising:
   an expandable outer sleeve member having an outer bone engaging surface comprising a helical thread for fixedly engaging with bone or tissue and an interior surface defining a first longitudinally extending passage;
   a first radially expandable portion of the outer sleeve member that extends about a portion of the first longitudinally extending passage and including at least a portion of the helical thread for engaging with a first bone or tissue of the synovial joint;
   an inner sleeve member having an outer surface and a leading distal portion configured to fit within and pass through the first longitudinally extending passage without expanding the first radially expandable portion of the outer sleeve member and a trailing proximal portion enlarged relative to the distal portion to engage with the first radially expandable portion of the outer sleeve member to urge the first radially expandable portion radially outward, and an interior surface defining a second longitudinally extending passage;
   a second radially expandable portion of the inner sleeve member for engaging with a second bone or tissue of the synovial joint;
   an expansion member having a body which is sized and configured to fit within the second longitudinally extending passage of the inner sleeve member and an outer surface portion configured to engage with the second radially expandable portion of the inner sleeve member to urge the second expandable portion radially outward.

2. The fastener of claim 1, wherein the outer surface of the inner sleeve member comprises a helical thread for fixedly engaging with the bone or tissue of the synovial joint.

3. The fastener of claim 2, wherein the second radially expandable portion of the inner sleeve member comprises at least a portion of the helical thread for fixedly engaging with the bone or tissue of the synovial joint.

4. The fastener of claim 1, wherein the interior surface of the inner sleeve member comprises a helical threaded portion and the expansion member comprises a threaded outer surface portion configured for threadingly engaging with the threaded portion of the inner sleeve member.

5. The fastener of claim 1, wherein the expandable outer sleeve comprises an abutment surface at a distal end thereof configured to abuttingly engage a surface of the adjacent second bone or tissue.

6. The fastener of claim 1, wherein the distal portion of the inner sleeve member comprises a tapered shaft portion.

7. The fastener of claim 1, wherein the relatively enlarged proximal portion of the inner sleeve member comprises an unthreaded shaft portion configured to engage with and expand the first radially expandable portion of the outer sleeve member.

8. The fastener of claim 1, wherein the outer sleeve member comprises a radially enlarged flange including an abutment surface for abutting against an exterior surface of the first bone to keep the outer sleeve member from being completely inserted within the first bone.

9. The fastener of claim 1, wherein the outer bone engaging surface of the expandable outer sleeve member has a length along a longitudinal axis thereof and the first radially expandable portion extends along at least a majority of the length of the outer bone engaging surface for securing the outer sleeve member to bone or tissue of the synovial joint.

* * * * *